(12) United States Patent
Takaoka et al.

(10) Patent No.: US 7,361,758 B2
(45) Date of Patent: Apr. 22, 2008

(54) CRYSTALS OF TRIAZASPIRO[5.5]UNDECANE DERIVATIVE

(75) Inventors: Yoshikazu Takaoka, Mishima-gun (JP); Masaki Okamoto, Suita (JP); Yuuichi Genba, Sakai-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 248 days.

(21) Appl. No.: 10/527,193

(22) PCT Filed: Sep. 17, 2003

(86) PCT No.: PCT/JP03/11835

§ 371 (c)(1),
(2), (4) Date: Mar. 10, 2005

(87) PCT Pub. No.: WO2004/026874

PCT Pub. Date: Apr. 1, 2004

(65) Prior Publication Data

US 2006/0052407 A1 Mar. 9, 2006

(30) Foreign Application Priority Data

Sep. 18, 2002 (JP) .............................. 2002-272079

(51) Int. Cl.
*C07D 471/10* (2006.01)
*A61K 31/499* (2006.01)

(52) U.S. Cl. .................. 544/231; 514/253.01

(58) Field of Classification Search ........... 514/253.01; 544/231

See application file for complete search history.

(56) References Cited

U.S. PATENT DOCUMENTS 7,053,090 B2 * 5/2006 Habashita et al. ..... 514/253.01
7,285,552 B2 10/2007 Mitsuya et al.
2005/0267114 A1 12/2005 Takaoka et al.
2006/0099170 A1 * 5/2006 Redfield et al. ........... 424/85.1

FOREIGN PATENT DOCUMENTS

| EP | 1 378 509 A1 | 1/2004 |
|---|---|---|
| EP | 1 541 574 A1 | 6/2005 |
| EP | 1 570 860 A1 | 9/2005 |
| EP | 1 623 721 A1 | 2/2006 |
| WO | WO 01/40227 A1 | 6/2001 |
| WO | 02/074769 A1 | 9/2002 |
| WO | WO 02/074770 A | 9/2002 |
| WO | WO 02/074770 A1 | 9/2002 |
| WO | WO 03/035074 A1 | 5/2003 |

OTHER PUBLICATIONS

Formaggio, F., "Nitroxyl peptides catalysts for enantioselective oxidations", Chemistry-A European Journal, (2002), vol. 8, No. 1, pp. 84 to 93.
International Search Report for PCT/JP03/11835 dated Dec. 9, 2003.
Supplementary European Search Report, dated Mar. 30, 2007 European Patent Office.

* cited by examiner

*Primary Examiner*—Charanjit S. Aulakh
(74) *Attorney, Agent, or Firm*—Sughrue Mion, PLLC

(57) ABSTRACT

The present invention relates to a new crystal of triazaspiro [5.5]undecane derivatives. The crystal of a non-solvate of (3R)-1-butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane hydrochloride have safety as drug substance, and have possibility to supply at large scale. And the crystal have an antagonistic activity against the interaction between chemokine and chemokine receptor, therefore, it is useful for manufacture of an agent for treating and/or preventing diseases such as various inflammatory diseases, asthma, atopic dermatitis, nettle rash, allergy disease, nephritis, nephropathy, hepatitis, arthritis, chronic rheumatoid arthritis, autoimmune disease, transplanted organ rejection reactions, acquired immunodeficiency syndrome and the like.

26 Claims, 32 Drawing Sheets

CRYSTALS OF TRIAZASPIRO[5.5]UNDECANE DERIVATIVE

This application is a 371 of PCT/JP03/11835 filed Sep. 17, 2003 which claims priority to JAPAN 2002-272079 filed Sep. 18, 2002.

TECHNICAL FIELD

The present invention relates to crystals of (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane hydrochloride (hereinafter sometimes referred to as Compound (I)), a process for producing the same and an agent containing the crystal as an active ingredient.

BACKGROUND ART

Chemokine is known as a basic protein having endogeneous leukocyte chemotactic and activating abilities and strong heparin-binding abilities. At present, it is considered that chemokine is related to not only the control of infiltration of specific leukocyte at the time of inflammations and immune responses but also the development and homing of lymphocyte under physiological conditions and migration of hemocyte precursor cells and somatic cells.

Differentiation, proliferation and cell death of hemocytes are controlled by various types of cytokine. In the living body, inflammations are found topically and differentiation, maturation and the like of lymphocytes are carried out at certain specified sites. That is, various necessary cells migrate into certain specified sites and accumulate therein to cause a series of inflammations and immune responses. Accordingly, migration of cells is also an indispensable phenomenon in addition to differentiation, proliferation and death of cells.

Migration of hemocytes in the living body starts firstly in the development stage by the shift of hematopoiesis started in the AGM region into permanent hematopoiesis in bone marrow via fetal liver. Furthermore, precursor cells of T cells and thymus dendritic cells migrate from the fetal liver into the bone marrow and then into the thymus gland and cytodifferentiate under thymus environment. The T cell which received clone selection migrates into secondary lymphoid tissues and takes part in an immune response in the periphery. The Langerhans' cell of the skin activated and differentiated by capturing an antigen migrates into the T cell region of a topical lymph node and activates naive T cell therein as a dendritic cell. The memory T cell performs its homing again into the lymph node via lymphatic and blood vessels. Also, B cell, T cell in the intestinal epithelium, γδ T cell, NKT cell and dendritic cell migrate from bone marrow without passing through the thymus gland and differentiate to take part in an immune response.

Chemokine is deeply related to the migration of these various cells. For example, MIP3β, SLC and its receptor CCR7 play an important role in the migration and homing of naive T cell, memory T cell and the mature dendritic cell which captured an antigen into a topical lymphoid tissue for the dendritic cells to encounter efficiently with the T cells. The T cell and dendritic cell necessary for controlling antigen-specific immune responses are hardly observed in the secondary lymph node of a PLT mouse having deficiency in the expression of SLC (*J. Exp. Med.*, 189(3), 451 (1999)).

MDC, TARC and its receptor CCR4 play an important role in the migration of Th2 cell into topical sites in immune and inflammatory responses in which the Th2 cell is related. In a rat fulminant hepatitis model (*P. acnes*+LPS), an anti-TARC antibody suppressed increase of the amount of ALT in blood and increase of the expressing amounts of TNFα and FasL in the liver and also improved lethality of the rats (*J. Clin. Invest.*, 102, 1933 (1998)). Also, an anti-MDC antibody decreased the number of eosinophils accumulated in the lung interstitium and suppressed airway hypersensitivity in a mouse OVA-induced airway hypersensitivity model (*J. Immunology*, 163, 403 (1999)).

MCP-1 and its receptor CCR2 are related to the infiltration of macrophage into inflammation sites. An anti-MCP-1 antibody showed an effect to suppress infiltration of monocyte and macrophage into glomerulus in a rat anti-Thy1.1 antibody glomerular nephritis model (*Kidney Int.*, 51, 770 (1997)).

Thus, chemokine receptors are greatly related to the control of inflammation and immune responses through a mechanism in which they are expressed at certain specified periods in variously specific cells and the effector cells are accumulated in a region where chemokine is produced.

Acquired immunodeficiency syndrome (called AIDS) which is induced by human immunodeficiency virus (hereinafter referred to as "HIV") is one of the diseases of which their therapeutic methods are most earnestly desired in recent years. Once infection with HIV is completed in a CD4-positive cell which is a principal target cell, HIV repeats its proliferation in the body of the patient and, sooner or later, completely destroys T cell which takes charge of the immunological function. During this process, the immunological function is gradually reduced to cause fever, diarrhea, lymph node enlargement and the like various immunodeficiency conditions which are apt to cause complications with *pneumocystis carinii* pneumonia and the like various opportunistic infections. Such conditions are the onset of AIDS, and it is well known that they induce and worsen Kaposi sarcoma and the like malignant tumors.

As the recent preventive and therapeutic methods for AIDS, attempts have been made to, e.g., (1) inhibit growth of HIV by the administration of a reverse transcriptase inhibitor or a protease inhibitor and (2) prevent or alleviate opportunistic infections by the administration of a drug having immunopotentiation activity.

Helper T cells which take charge of the central of immune system are mainly infected with HIV. It is known since 1985 that HIV uses the membrane protein CD4 expressing on the membrane of T cells in the infection (*Cell*, 52, 631 (1985)). The CD4 molecule is composed of 433 amino acid residues, and its expression can be found in macrophages, some B cells, vascular endothelial cells, Langerhans' cells in skin tissues, dendritic cells in lymphoid tissues, glia cells of the central nervous system and the like, in addition to the mature helper T cells. However, since it has been revealed that the infection with HIV is not completed by the CD4 molecule alone, a possibility has been suggested on the presence of factors other than the CD4 molecule, which are related to the infection of cells with HIV.

In 1996, a cell membrane protein called Fusin was identified as a factor other than the CD4 molecule, which is related to the HIV infection (*Science*, 272, 872 (1996)). It was confirmed that this Fusin molecule is a receptor (namely, CXCR4) of stromal derived factor-1 (hereinafter referred to as "SDF-1"). In addition, it was confirmed also in vitro that the SDF-1 specifically inhibits infection of T cell tropic (X4) HIV (*Nature*, 382, 829 (1996), *Nature*, 382, 833 (1996)). That is, it is considered that the HIV infection was inhibited by the binding of SDF-1 to CXCR4 preceding HIV, thereby depriving HIV of a foothold for infecting cells.

Also at that time, it was discovered that another chemokine receptor CCR5, which is a receptor of RANTES, MIP-1α and MIP-1β, is also used at the time of the infection with a macrophage tropic (R5) HIV (*Science*, 272, 1955 (1996)).

Accordingly, substances which can compete with CXCR4 and CCR5 for HIV, or which can bind to HIV virus thus causing the virus unable to bind to CXCR4 and CCR5, could become HIV infection inhibitors. Also, there is a case in which a low molecular compound initially discovered as an HIV infection inhibitor was actually a CXCR4 antagonist (*Nature Medicine*, 4, 72 (1998)).

Based on the above, it is considered that the chemokine/chemokine receptors are deeply related to the inflammation, immune disease or HIV infection. For example, it is considered that they are related to various inflammatory diseases, asthma, atopic dermatitis, nettle rash, allergic diseases (allergic bronchopulmonary aspergillosis, allergic eosinophilic gastroenteritis and the like), nephritis, nephropathy, hepatitis, arthritis, chronic rheumatoid arthritis, psoriasis, rhinitis, conjunctivitis, ischemia-reperfusion injury, multiple sclerosis, ulcerative colitis, acute respiratory distress syndrome, shock accompanied by bacterial infection, diabetes mellitus, autoimmune diseases, graft versus host disease, immunosuppression, metastasis, acquired immunodeficiency syndrome and the like.

Previously, it is reported that triazaspiro[5.5]undecane derivatives have an antagonize effect of chemokine/chemokine receptor, so they are used for prevention and/or treatment of diseases which are concerned in chemokines, such as various inflammatory diseases, asthma, atopic dermatitis, urticaria, allergic diseases (allergic bronchopulmonary aspergillosis or allergic eosinophilic gastroenteritis etc.), nephritis, nephropathy, hepatitis, arthritis, rheumatoid arthritis, psoriasis, rhinitis, conjunctivitis, ischemic reperfusion disorder, multiple sclerosis, ulcerative colitis, acute respiratory distress syndrome, cytotoxic shock, diabetes, autoimmune disease, transplanted organ rejection reactions, immunosuppression, cancer metastasis and acquired immune deficiency syndrome(ref specification of WO01/40227).

However, the specification does not at all disclose Compound (I) and Compound (I) is a novel compound.

DISCLOSURE OF THE INVENTION

Compound (I) is described in Example 9(54) of WO 02/074770. According to the investigations made by the present inventors, however, it was found that Compound (I) produced by the method described in the specification was not crystal but amorphous.

Generally, amorphous substances have the following problems for use as drug substances of pharmaceutical products. For practical production of pharmaceutical products using such amorphous substances and marketing of the resulting pharmaceutical products, potentially, the resulting pharmaceutical products may not retain consistent quality. Unless a pharmaceutical product with great pharmaceutical effects and a certified safety profile can retain consistent quality, such a pharmaceutical product rather may cause adverse events and has no significance of existence as a pharmaceutical. For pharmaceutical products, it is one of greatly important issues to retain the quality. For securing this quality, it is required to maintain a stable supply of drug substance with consistent quality at any time. Supply of a drug substance not amorphous but crystal is a very effective method.

Since Compound (I) produced according to the method described in the specification of WO 02/074770 is amorphous, it is very difficult to supply the compound as a compound having consistent quality consistently at a large scale. Therefore, the drug substance obtained by the method has a serious disadvantage for practical supply as a pharmaceutical product. Accordingly, stable single crystals of Compound (I) having consistent quality and being possibly supplied as pharmaceutical drug substance at a large scale have been desired.

In order to obtain such crystals of Compound (I), the inventors made investigations. First, the free form of Compound (I), i.e. (3R)-1-butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane was dissolved in a mixed solvent of hydrochloric acid (namely, aqueous hydrogen chloride solution) and methanol, the resulting mixture was agitated at 50 to 55° C., cooled to room temperature, and further cooled to 0 to 5° C., and the resulting precipitated solid was filtered. Unexpectedly, however, the analysis of the solid demonstrated that the solid contained the solvent components (Solid B described below). Solid B was analyzed by X ray crystal diffractometry at room temperature. However, Solid B never consistently gave an identical X ray crystal diffraction spectrum. Therefore, no clear structure analysis could be obtained. The results of the analysis by X ray crystal diffractometry at low temperature suggested that Solid B might be a solvate of methanol and water. As described above, it was found that it was difficult to obtain crystals of a non-solvate of Compound (I) by general crystallization procedures. Hence, it was assumed that Compound (I) might be a compound to be very readily solvated. For use as a drug substance for pharmaceutical products, such a solvate may sometimes cause problems from the standpoints of safety and toxicity. For example, the mass weight of some hydrates may change due to its hygroscopicity and the release of $H_2O$ molecule, while methanol solvates can never be used as pharmaceutical drug substances because of the toxicity of methanol.

In order to overcome these problems, the inventors made further investigations. Consequently, the inventors made a success in the production of pure homogenous crystals of a non-solvate of Compound (I) and also successfully established a method for crystallizing them. Thus, the invention has been achieved.

The crystals of a non-solvate of Compound (I) in accordance with the invention (hereinafter sometimes referred to as "the crystals of a non-solvate of Compound (I)") is not described in WO 02/074770. Specifically, the crystals of a non-solvate of Compound (I) apparently differ from the compound produced according to the method described in Example 9(54) of WO 02/074770, in view of the data recovered by X ray crystal diffractometry, differential scanning calorimetry (DSC), and IR absorptiometry. Thus, the crystals of a non-solvate of Compound (I) are novel crystals of the compound.

Additionally, the inventors successfully obtained the crystals of a non-solvate of Compound (I) from the solvate of Compound (I) or the amorphous Compound (I).

That is, the present invention relates to the followings and the like:

[1] A crystal of (3R)-1-butyl-2,5-dioxo-3-[(1R)-1-hydroxy-1-cyclohexylmethyl]-9-[4-(4-carboxyphenyloxy)phenyl methyl]-1,4,9-triazaspiro[5.5]undecane hydrochloride.

[2] The crystal according to the above [1], which is a non-solvate.

[3] The crystal according to the above [1], which has a melting point of about 230° C. to about 240° C.

[4] The crystal according to the above [1], which has a melting point of about 232° C. to about 235° C.

[5] The crystal according to the above [1], which has a powdery X ray diffraction spectrum shown in FIG. 1.

[6] The crystal according to the above [5], which has diffraction angle 2θ of 5.15, 8.06, 10.26, 11.01, 13.72, 15.46, 17.36, 18.03, 18.58, 19.00, 19.51, 20.71, 21.73, 22.58, 23.80, 24.96 and 27.07(degree) on the powdery X ray diffraction spectrum.

[7] The crystal according to the above [1], which has an IR absorption spectrum shown in FIG. 3.

[8] The crystal according to the above [7], which has absorptions at 2924, 2504, 1682, 1632, 1597, 1503, 1426, 1377, 1235, 1163, 1098, 961, 928, 876, 855, 770, 727 and 681 $cm^{-1}$ on the IR absorption spectrum.

[9] The crystal according to the above [1], which has a mean particle size of about 0.05 μm to about 200 μm.

[10] The crystal according to the above [2], which is a crystal of $P2_1$ space group.

[11] The crystal according to the above [10], which has lattice constants of a=11.8105 Å±7%, b=7.8730 Å±7% and c=18.2351 Å±7%.

[12] The crystal according to the above [2], which is substantially free of a lower alcohol solvent or a water-miscible ether solvent or contains it in a residual amount of 5,000 ppm or less.

[13] A process for producing a crystal of a non-solvate of (3R)-1-butyl-2,5-dioxo-3-((1R)-1-hydroxy-1-cyclohexyl-methyl)-9-(4-(4-carboxyphenyloxy)phenylmethyl)-1,4,9-triazaspiro[5.5]undecane hydrochloride, which comprises carrying out crystallization from a lower alcohol solvent which may contain water or a water-miscible ether solvent which may contain water, in which a crudely purified substance of (3R)-1-butyl-2,5-dioxo-3-((1R)-1-hydroxy-1-cyclohexylmethyl)-9-(4-(4-carboxyphenyloxy)phenyl-methyl)-1,4,9-triazaspiro[5.5]undecane hydrochloride is dissolved or suspended.

[14] The process according to the above [13], wherein the lower alcohol solvent is $C_{1-4}$ alkyl alcohol or $C_{1-4}$ alkyl acetate.

[15] The process according to the above [14], wherein the lower alcohol solvent is methanol or ethanol.

[16] The process according to the above [14], wherein the lower alcohol solvent is ethyl acetate.

[17] The process according to the above [13], wherein the water-miscible ether solvent is 1,2-dimethoxyethane, dioxane or tetrahydrofuran.

[18] The process according to the above [13], wherein the water and the lower alcohol solvent or the water and the water-miscible ether solvent are mixed in a mixing volume ratio of 1:50 to 7:3.

[19] The process according to the above [18], wherein the water and the lower alcohol solvent or the water and the water-miscible ether solvent are mixed in a mixing volume ratio of 1:35 to 5:5.

[20] The process according to the above [13], wherein the crystallization is carried out at about −10° C. to about 40° C.

[21] The process according to the above [13], wherein the crystallization is carried out for about 20 minutes to about 5 hours.

[22] A crystal of a non-solvate of (3R)-1-butyl-2,5-dioxo-3-((1R)-1-hydroxy-1-cyclohexylmethyl)-9-(4-(4-carboxy-phenyloxy)phenylmethyl)-1,4,9-triazaspiro[5.5]undecane hydrochloride which is obtainable by the process according to any one of above [13] to [21].

[23] A process for producing a crystal of a non-solvate of (3R)-1-butyl-2,5-dioxo-3-((1R)-1-hydroxy-1-cyclohexyl-methyl)-9-(4-(4-carboxyphenyloxy)phenylmethyl)-1,4,9-triazaspiro [5.5]undecane hydrochloride, which comprises: dissolving or suspending (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5] undecane and hydrogen chloride in a solvent selected from (1) $C_{1-4}$ alkyl alcohol, (2) a mixed solvent of $C_{1-4}$ alcohol and water, (3) a water-miscible ether solvent, (4) a mixed solvent of a water-miscible ether solvent and water, (5) a mixed solvent of $C_{1-4}$ alkyl alcohol and a water-miscible ether solvent, (6) a mixed solvent of $C_{1-4}$ alkyl alcohol, a water-miscible ether solvent and water and (7) water, followed by heating at about 40° C. to about 80° C.; and cooling the resulting mixture at about −5° C. to about 35° C.

[24] The process according to the above [23], wherein the $C_{1-4}$ alcohol is methanol or ethanol.

[25] The process according to the above [23], wherein the water-miscible ether solvent is 1,2-dimethoxyethane, dioxane or tetrahydrofuran.

[26] The process according to the above [23], which comprises: dissolving or suspending (3R)-1-butyl-2,5-dioxo-3-((1R)-1-hydroxy-1-cyclohexylmethyl)-9-(4-(4-carbox-yphenyloxy)phenylmethyl)-1,4,9-triazaspiro[5.5] undecane and hydrogen chloride in a solvent selected from (1) $C_{1-4}$ alkyl alcohol, (2) a mixed solvent of $C_{1-4}$ alcohol and water, (3) a water-miscible ether solvent, (4) a mixed solvent of a water-miscible ether solvent and water, (5) a mixed solvent of $C_{1-4}$ alkyl alcohol and a water-miscible ether solvent, (6) a mixed solvent of $C_{1-4}$ alkyl alcohol, a water-miscible ether solvent and water and (7) water, followed by heating at about 40° C. to about 80° C.; cooling the resulting mixture at about −5° C. to about 35° C.; adding $C_{1-4}$ alcohol or a water-miscible ether solvent to the mixture; and optionally adding water to the mixture.

[27] A process for producing a crystal of a non-solvate of (3R)-1-butyl-2,5-dioxo-3-((1R)-1-hydroxy-1-cyclohexyl-methyl)-9-(4-(4-carboxyphenyloxy)phenylmethyl)-1,4,9-triazaspiro[5.5]undecane hydrochloride, which comprises dissolving or suspending a solvate of (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5] undecane hydrochloride or amorphous (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5] undecane hydrochloride in $C_{1-4}$ alkyl acetate, followed by heating at about 40° C. to about 80° C.; and cooling the resulting mixture at about −5° C. to about 35° C.

[28] A crystal of a non-solvate of (3R)-1-butyl-2,5-dioxo-3-((1R)-1-hydroxy-1-cyclohexylmethyl)-9-(4-(4-car-boxy-phenyloxy)phenylmethyl)-1,4,9-triazaspiro[5.5]un-decane hydrochloride which is obtainable by the process according to any one of above [20] to [24].

[29] The crystal according to the above [28], which has a mean particle size of about 0.05 μm to about 200 μm.

[30] A pharmaceutical composition comprising the crystal according to the above [1], [22] or [28] as an active ingredient.

[31] The pharmaceutical composition according to the above [30], which is a regulator of interaction between chemokine and a chemokine receptor.

[32] The pharmaceutical composition according to the above [31], which is an agent for treating and/or preventing diseases caused by interaction between chemokine and a chemokine receptor.

[33] A method for treating and/or preventing diseases caused by interaction between chemokine and a chemokine receptor in a mammal, which comprises administering to a mammal an effective amount of the crystal according to the above [1], [22] or [28]; and

[34] Use of the crystal according to the above [1], [22] or [28] in the manufacture of an agent for treating and/or preventing diseases caused by interaction between chemokine and a chemokine receptor.

Crystals of a non-solvate of Compound (I), i.e. crystals of a non-solvate of (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane hydrochloride, are characterized by the following powder X-ray diffraction spectral data, infrared (IR) absorption spectral data, data for differential scanning calorimetry and the like.

Crystals of a non-solvate of (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane hydrochloride showing a diffraction angle (2θ), a half-value width and a relative intensity in powder X-ray diffraction spectrum using Cu—Kα ray are as shown in Table 1 (hereinafter sometimes referred to as Crystal A).

TABLE 1

| diffraction angle (2θ) | half-value width | relative intensity |
|---|---|---|
| 5.15 | 0.22 | High |
| 8.06 | 0.22 | Moderate |
| 10.26 | 0.26 | Moderate |
| 11.01 | 0.23 | Moderate |
| 13.72 | 0.39 | High |
| 15.46 | 0.74 | Moderate |
| 17.36 | 0.24 | Moderate |
| 18.03 | 0.22 | Moderate |
| 18.58 | 0.23 | Slightly high |
| 19.00 | 0.21 | Slightly high |
| 19.51 | 0.20 | Moderate |
| 20.71 | 0.19 | Moderate |
| 21.73 | 0.25 | Moderate |
| 22.58 | 0.36 | Moderate |
| 23.80 | 0.34 | Moderate |
| 24.96 | 0.61 | Moderate |
| 27.07 | 0.45 | Moderate |

Crystals of a non-solvate of (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane hydrochloride having absorptions at 2924, 2504, 1682, 1632, 1597, 1503, 1426, 1377, 1235, 1163, 1098, 961, 928, 876, 855, 770, 727 and 681 $cm^{-1}$ on infrared (IR) absorption spectrum.

Crystals of a non-solvate of (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane hydrochloride having an endothermic peak around 244° C. on differential scanning calorimetry.

The crystals of a non-solvate Compound (I) in accordance with the invention are identified by the physicochemical properties in this specification. However, the physicochemical properties vary more or less due to the characteristics of these spectral data. Therefore, the physicochemical properties should not be strictly understood.

For example, the diffraction angle (2θ), half width and overall pattern of powdery X ray diffraction spectrum are important for crystal identification. The relative intensity may vary more or less, depending on the direction of crystal growth, the particle size and the measuring conditions, because of the data properties obtained by powdery X ray diffractometry.

Additionally, overall differential scanning calorimetric pattern is important for crystal identification, and may vary more or less, depending on the measuring conditions.

Furthermore, overall IR absorption spectral pattern is important for crystal identification, and may more or less vary, depending on the measuring conditions.

In the present specification, the solid in which methanol and water are solvated to Compound (I), i.e. Solid B which will be described later, is specified by the physicochemical properties in the present specification and there is no limitation for the process of producing the same. Thus, so long as it is a solid which shows the differential scanning colorimetric data and/or infrared absorption spectral data of Solid B described in Examples which will be given later, any solid which is produced by any producing process is included in Solid B. However, since there will be some changes in view of properties of the data of each spectrum, the above should not be interpreted strictly.

In the present specification, the solid in which ethanol and/or water are solvated to Compound (I), i.e. Solid C which will be described later, is specified by the physicochemical properties in the present specification and there is no limitation for the process of producing the same. Thus, so long as it is a solid which shows the differential scanning colorimetric data and/or infrared absorption spectral data of Solid C described in the Examples which will be given later, any solid which is produced by any producing process is included in Solid C. However, since there will be some changes in view of properties of the data of each spectrum, the above should not be interpreted strictly.

In the present specification, amorphous Compound (I) is specified by the physicochemical properties in the present specification and there is no limitation for the process of producing the same to the process described in the specification of WO 02/074770. Thus, so long as it is an amorphous compound which shows the differential scanning calorimetric data and/or infrared absorption spectral data of Compound (I) described in the Examples which will be given later, any amorphous compound which is produced by any producing process is covered as amorphous Compound (I). However, since there will be some changes in view of properties of the data of each spectrum, the above should not be interpreted strictly.

In the present specification, a crudely purified substance of Compound (I) is one which contains Compound (I) as a component and does not show the physicochemical properties of the present specification which are shown by the crystals of the non-solvate of Compound (I).

In the present specification, crystals of Compound (I) include all crystals so long as they are crystals of Compound (I) and are regardless of absence or presence of solvation. Thus, they may be either crystals in which a solvent is solvated to Compound (I) or crystals of a non-solvate of Compound (I). Here, with regard to the crystals of Compound (I), crystals of a non-solvate of Compound (I) are preferred. The crystals of a non-solvate of Compound (I) are preferably crystals having a mean particle size applicable as pharmaceutical drug substances. Specifically, the mean particle size of the crystals is preferably about 0.05 μm to about 200 μm, more preferably about 1 μm to about 50 μm, and particularly preferably about 5 μm to about 30 μm. The particle size is most preferably about 10 μm to about 20 μm.

Crystals of a non-solvate of Compound (I) of the present invention mean crystals which are not substantially solvated. Crystals which are not substantially solvated mean that no solvent component is contained in the crystal lattice thereof and also include those where a solvent component is contained outside the crystal lattice. Thus, crystals of a non-solvate of Compound (I) also include, for example, crystals in which a solvent component is contained outside the crystal lattice.

In addition, the crystals of a non-solvate of Compound (I) of the present invention may contain non-crystals within an allowable range or solid of solvate within an allowable range (e.g., the above-described Solid B, Solid C, solvated solids other than them, etc.).

As described above, crystals of the non-solvate of Compound (I) of the present invention include those where a solvent component is contained outside the crystal lattice and/or those where solid of the solvate within an allowable range is mixed. Although the amount of the solvent component (which may be called residual amount or solvent residue amount) varies depending upon the solvent, the amount is preferably to be an amount of the solvent component within an allowable range as the material for medicaments. For example, it is preferred that low alcohol solvent or water-miscible ether solvent is not substantially contained or is not more than about 5,000 ppm as the residual amount. More specifically, in the case of methanol, for example, it is preferred that the solvent residue amount in the crystals of the non-solvate of Compound (I) of the present invention is within a range of from about 0 ppm to about 3,000 ppm, preferably from about 0 ppm to about 2,000 ppm or, more preferably, from about 0 ppm to about 1,500 ppm and, in the case of ethyl acetate, for example, it is preferred that it is within a range of from about 0 ppm to about 5,000 ppm. A water content is preferably about 1% or less.

Crystals of a non-solvate of Compound (I) are crystals of a $P2_1$ space group and the lattice constants thereof are a=11.8105 Å, b=7.8730 Å and c=18.2351 Å. Here, the lattice constants represented by a, b and c increase or decrease by influence of temperature for example and, therefore, they are not to be interpreted strictly. It is preferred that changes of each of the lattice constants a, b and c are within about ±15%, more preferably within about ±7% and particularly preferably within about ±5%.

Crystals of a non-solvate of Compound (I) have a melting point of about 225° C. or more. More specifically, crystals of a non-solvate of Compound (I) have a melting point of about 230° C. to about 240° C., and preferably about 232° C. to about 235° C. The melting point can be confirmed by a commonly conducted method for measurement of a melting point but, since it is changeable to some extent due to the measuring conditions, that is not to be interpreted strictly.

Method for Producing the Inventive Compound:

Crystals of (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane hydrochloride can be produced by the methods which will be described below, by methods similar thereto or by the methods described in the Examples. More specifically, crystals of a non-solvate of (3R)-1-butyl-2,5-dioxo-3-((1R)-1-hydroxy-1-cyclohexylmethyl)-9-(4-(4-carboxy-phenyloxy)phenylmethyl)-1,4,9-triazaspiro[5.5]undecane hydrochloride of the present invention can be produced by the reaction of the following Method 1 to Method 4.

Method 1:

A process in which a free form of Compound (I) is subjected to a conversion reaction to a hydrochloride and then crystals of a non-solvate of Compound (I) is obtained without isolation and purification.

Method 2:

A method in which a free form of Compound (I) is subjected to a conversion reaction to a hydrochloride, a solvate (Solid B which will be described later) of Compound (I) is isolated and purified and then crystals of a non-solvate of Compound (I) are obtained.

Method 3:

A method in which a free form of Compound (I) is subjected to a conversion reaction to a hydrochloride, a solvate (Solid C which will be described later) of Compound (I) is isolated and purified and then crystals of a non-solvate of Compound (I) are obtained.

Method 4:

A method in which a free form of Compound (I) is subjected to a conversion reaction to a hydrochloride, amorphous Compound (I) is isolated and purified (being carried out according to a method described in Example 9(54) of WO 02/074770) and then crystals of a non-solvate of Compound (I) are obtained.

Hereinafter, each of the methods will be illustrated in detail.

(1) Method 1 is a process for producing crystals of a non-solvate of Compound (I) of the present invention in which (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane is subjected to a conversion reaction to a hydrochloride, followed by crystallization without isolation and purification.

The conversion reaction to a hydrochloride is known and, for example, it is carried out in a solvent containing hydrogen chloride at a temperature of about 0° C. to about 90° C. or preferably about 40° C. to about 80° C. The solvent for "the solvent containing hydrogen chloride" may be a solvent in which hydrogen chloride is able to be dissolved or a solvent which is miscible with a solvent in which hydrogen chloride is able to be dissolved. A solvent containing hydrogen chloride can be easily prepared in such a manner that hydrogen chloride gas or an aqueous hydrogen chloride solution, i.e. hydrochloric acid, is added to a solvent in which hydrogen chloride is able to be dissolved or a solvent which is miscible with a solvent in which hydrogen chloride is able to be dissolved. The solvent for "the solvent containing hydrogen chloride" includes (1) $C_{1-4}$ alkyl alcohol, (2) a mixed solvent of $C_{1-4}$ alcohol and water, (3) a water-miscible ether solvent, (4) a mixed solvent of a water-miscible ether solvent and water, (5) a mixed solvent of $C_{1-4}$ alkyl alcohol and a water-miscible ether solvent, (6) a mixed solvent of $C_{1-4}$ alkyl alcohol, a water-miscible ether solvent and water and (7) water. The solvent for "a solvent containing hydrogen chloride" is preferred to be a solvent which is also able to be used as a solvent in crystallization being carried out after the conversion reaction to a hydrochloride. The solvent includes "an optionally water-containing lower alcohol solvent or a water-miscible ether solvent". The "lower alcohol solvent" includes $C_{1-4}$ alkyl alcohol (e.g., methanol, ethanol, propanol, isopropanol, butanol, sec-butyl alcohol, tert-butyl alcohol, etc.) and acetic acid ester of $C_{1-4}$ alkyl alcohol or $C_{1-4}$ alkyl acetate (e.g., methyl acetate, ethyl acetate, propyl acetate, isopropyl acetate, butyl acetate, sec-butyl acetate, tert-butyl acetate, etc.). The "water-miscible ether solvent" includes 2-dimethoxyethane, dioxane and tetrahydrofuran. The "lower alcohol solvent or water-miscible ether solvent which may contain water" as a solvent in the conversion reaction to a hydrochloride is preferably a mixed solvent of water and the above-described "$C_{1-4}$ alkyl alcohol", or a mixed solvent of water and the above-described "water-miscible ether solvent". It is more preferably a mixed solvent of water and methanol, a mixed solvent of water and ethanol and a mixed solvent of water and dioxane and particularly preferably a mixed solvent of water and methanol.

The crystallization is carried out by stirring a reaction mixture solution for subjecting to a conversion reaction to a hydrochloride at about −10° C. to about 40° C. to crystallize Crystal A.

More specifically, after a conversion reaction to a hydrochloride is carried out at about 40° C. to about 80° C. using, for example, "a lower alcohol solvent or a water-miscible ether solvent which may contain water" containing hydrogen chloride, followed by stirring at about −10C to about 40° C., preferably at about −5° C. to about 35° C. or more preferably at about −5° C. to about 10° C., a treatment is carried out if necessary (such as that a lower alcohol solvent or a water-miscible ether solvent is added thereto) to separate Crystal A and a further treatment is carried out if necessary (such as that water is added thereto) to efficiently manufacture Crystal A, i.e. crystals of a non-solvate of Compound (I).

When the above-described "$C_{1-4}$ alkyl alcohol" is used, a solvated solid (such as Solid B or Solid C which will be described later) is produced and, therefore, in order to obtain Crystal A which are crystals of a non-solvate of the compound A in a stable manner, it is preferred that, after the conversion reaction to a hydrochloride, the above-described "$C_{1-4}$ alkyl alcohol" is added if necessary so that the mixing ratio by volume of water to the above-described "$C_{1-4}$ alkyl alcohol" is changed.

When the above-described "$C_{1-4}$ alkyl alcohol" or "water-miscible ether solvent" is used, it is preferred, if necessary, to add water for improving the yield of Crystal A which are crystals of a non-solvate of Compound (I).

Although there is no particular limitation for the mixing ratio by volume of water to the above-described "$C_{1-4}$ alkyl alcohol" or that of water to the above-described "water-miscible ether solvent" in the above-described Method 1, it is preferred to be within a range of 1:50 to 7:3 or more preferably 1:35 to 1:1.

(2) Method 2 is a process for producing crystals of a non-solvate of Compound (I) of the present invention in which (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane is subjected to a conversion reaction to a hydrochloride using a mixed solvent of methanol and water containing hydrogen chloride and a solvate (Solid B which will be described later) of Compound (I) is isolated and purified, followed by crystallization.

The conversion reaction to a hydrochloride is carried out in the same manner as in the conversion reaction to a hydrochloride in the above-described Method 1. More specifically, the conversion reaction to a hydrochloride is carried out at about 40° C. to about 80° C., followed by stirring at about −10° C. to about 35° C. or preferably at about −5° C. to about 10° C. to thereby separate a solid. The separated solid is isolated and purified by a method which has been commonly conducted by one skilled in the art (e.g., filtration, drying, etc.), followed by the following crystallization.

The crystallization is carried out by stirring the solid obtained in the above-described reaction at about 40° C. to about 80° C. or preferably at about 50° C. to about 80° C. using the above-described "lower alcohol solvent or water-miscible ether solvent which may contain water", etc., followed by stirring at about −5° C. to about 35° C. or preferably at about 10C to about 35° C. so as to separate the crystals. The "optionally water-containing lower alcohol solvent or water-miscible ether solvent" includes ethyl acetate, methanol, ethanol, 1,2-dimethoxyethane, and the like, or a mixed solvent thereof with water (e.g., aqueous methanol solution, aqueous ethanol solution, aqueous 1,2-dimethoxyethane solution, etc.). Ethyl acetate is particularly preferred. Although it is more preferred that the crystallization is carried out using a solvent which is free of water, it is also possible to use, if necessary, a mixed solvent of water and a lower alcohol solvent or a mixed solvent of water and a water-miscible ether solvent in any mixing ratio or preferably the mixed solvent having a water ratio of 25% or less.

(3) Method 3 is a process for producing crystals of a non-solvate of Compound (I) of the present invention in which (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane is subjected to a conversion reaction to a hydrochloride using a mixed solvent of ethanol and water containing hydrogen chloride and a solvate (Solid C which will be described later) of Compound (I) is isolated and purified, followed by crystallization.

The conversion reaction to a hydrochloride is carried out in the same manner as in the conversion reaction to a hydrochloride in the above-described Method 1. More specifically, the conversion reaction to a hydrochloride is carried out at about 40° C. to about 80° C., followed by stirring at about −10° C. to about 35° C. or preferably at about −5° C. to about 10C to thereby separate a solid. The separated solid is isolated and purified by a method which has been commonly conducted by one skilled in the art (e.g., filtration, drying, etc.) and subjected to the crystallization described in the above-described Method 2 to prepare crystals of a non-solvate of Compound (I) of the present invention.

(4) Method 4 is a process for producing crystals of a non-solvate of Compound (I) of the present invention in which (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane is subjected to a method described in Example 9(54) of WO 02/074770 to isolate and purify a non-crystals of Compound (I), followed by crystallization.

The conversion reaction to a hydrochloride and purifying method are carried out in the same manner as described in Example 9(54) of WO 02/074770. When the amorphous product obtained by that method is subjected to crystallization described in the above-described Method 2, it can be made into crystals of a non-solvate of Compound (I) of the present invention.

The conversion reaction to a hydrochloride and the crystallization are preferably carried out in a series of reactions in view of convenience in the operation.

In Method 2 to Method 4, methods for obtaining Solid B, Solid C or an amorphous product are disclosed but the method for preparing those solids or the amorphous product is not limited to those methods. Accordingly, even when Solid B, Solid C or the amorphous product prepared by any method is used, all of such a method is included within a scope of the present invention so far as the crystals of a non-solvate of Compound (I) of the present invention are obtained by the above-described method.

Even when a solvate or an amorphous product which is other than the above-described ones is obtained by a conversion reaction to a hydrochloride, it is possible to be made into crystals of a non-solvate of Compound (I) of the present invention by subjecting to the crystallization described in the above-described Method 2.

The product, (3R)-1-butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane, for use in the production of the inventive compound can be produced by subjecting (3R)-1-butyl-2,5-dioxo-3-[(1R)-1-hydroxy-1-cyclohexylmethyl]-1,4,9-triazaspiro[5.5]undecane or an acid addition salt thereof and 4-(4-formylphenyloxy)benzoic acid to a reductive amination.

The reductive amination is known and is carried out in the presence of a reducing agent (for example, sodium triacetoxyborohydride, and sodium cyanoborohydride) in the presence or absence of a tertiary amine (for example, triethylamine, and diisopropylethylamine) in an organic solvent (for example, dichloroethane, dichloromethane, dimethylformamide, acetic acid, and mixtures thereof) at a temperature of 0 to 40° C.

Furthermore, (3R)-1-butyl-2,5-dioxo-3-[(1R)-1-hydroxy-1-cyclohexylmethyl]-1,4,9-triazaspiro[5.5]undecane or an acid addition salt thereof can be produced by the following reaction scheme (I).

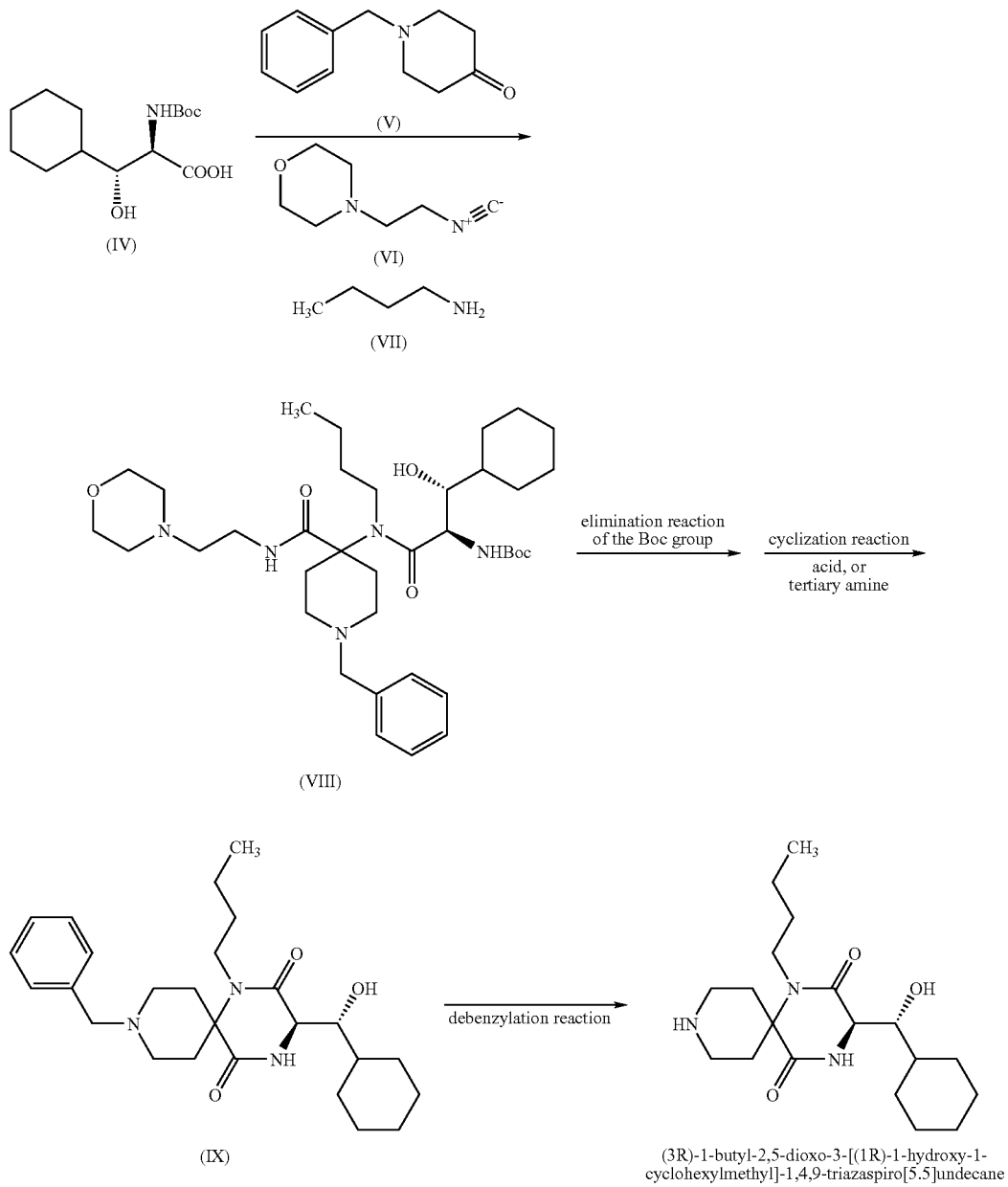

In the reaction scheme (I), the individual reactions are progressed by known processes. In the reaction scheme, further, compounds represented by formulae (IV), (V), (VI) and (VII) are known per se or can be produced readily by known processes. In this specification, the abbreviation "Boc" represents a tert-butoxycarbonyl group. The acid addition salt includes salts with inorganic acids (for example, hydrochloride, hydrobromide, hydroiodide, sulfate, phosphate, and nitrate), or salts with organic acids (for example, acetate, trifluoroacetate, lactate, tartrate, succinate, fumarate, maleate, benzoate, citrate, methanesulfonate, ethanesulfonate, benzenesulfonate, toluenesulfonate, isethionate, glucuronate, and gluconate).

Specifically, (3R)-1-butyl-2,5-dioxo-3-[(1R)-1-hydroxy-1-cyclohexylmethyl]-1,4,9-triazaspiro[5.5]undecane or an acid addition salt thereof can be produced by allowing the reaction of compounds represented by formulae (IV), (V), (VI) and (VII) to obtain a compound represented by formula (VIII), and then subjecting the compound of formula (VIII) to a elimination reaction of the Boc group, a cyclization reaction or, if necessary, a conversion reaction to an acid addition salt thereof, to obtain the compound represented by formula (IX) or an acid addition salt thereof, which is then subjected to debenzylation reaction.

More specifically, the compound of formula (VIII) can be obtained, for example, by heating compounds of formula (IV), (V), (VI) and (VII) in an organic solvent (for example, methanol and ethanol) to 30 to 100° C.

Furthermore, the compound of formula (IX) or an acid addition salt thereof can be produced by subjecting the compound of formula (VIII) to an elimination reaction of the Boc group, a cyclization reaction, and if necessary, a conversion reaction to an acid addition salt.

The elimination reaction of the Boc group is known and is carried out, for example, in an organic acid (for example, acetic acid, trifluoroacetic acid, methanesulfonic acid, and p-toluene sulfonic acid) or an inorganic acid (for example, hydrochloric acid, and sulfuric acid) or a mixture thereof (for example, hydrogen bromide/acetic acid) in an organic solvent (for example, dichloromethane, chloroform, dioxane, ethyl acetate, and anisole) at a temperature of 0 to 100° C.

Additionally, the cyclization reaction is known and carried out by heating to 60 to 120° C. in an organic solvent (for example, ethyl acetate, dichloroethane, and toluene), using tertiary amines (for example, triethylamine and diisopropylethylamine) or using or never using an acid (for example, acetic acid, and trifluoroacetic acid). The reaction involves breakage of morpholinoethylamino group, simultaneously with cyclization.

Furthermore, the conversion reaction to an acid addition salt is known and is carried out, for example, in the presence of acids [for example, inorganic acids (for example, hydrochloric acid, hydrobromic acid, hydroiodic acid, sulfuric acid, phosphoric acid, and nitric acid) or organic acids (for example, acetic acid, trifluoroacetic acid, lactic acid, tartaric acid, succinic acid, fumaric acid, maleic acid, benzoic acid, citric acid, methanesulfonic acid, ethanesulfonic acid, benzenesulfonic acid, toluenesulfonic acid, isethionic acid, glucuronic acid, and gluconic acid)] in an organic solvent (for example, methanol, ethanol, dioxane, ethyl acetate, and mixtures thereof) in the presence or absence of water at a temperature of 0 to 90° C. Then, the reaction mixture is further agitated at −10 to 40° C. to precipitated the crystals.

(3R)-1-Butyl-2,5-dioxo-3-[(1R)-1-hydroxy-1-cyclohexylmethyl]-1,4,9-triazaspiro[5.5]undecane or an acid addition salt thereof can be produced by subjecting the compound of the formula (IX) or an acid addition salt thereof to a debenzylation reaction. The debenzylation reaction is known and is carried out in the presence of a catalyst (for example, palladium/carbon, palladium black, palladium hydroxide, platinum oxide, and Raney-nickel) in a solvent [for example, ethers (for example, tetrahydrofuran, dioxane, dimethoxyethane, and diethyl ether), alcohols (for example, methanol, and ethanol), benzenes (for example, benzene, and toluene), ketones (for example, acetone, and methyl ethyl ketone), nitrites (for example, and acetonitrile), amides (for example, dimethylformamide), water, ethyl acetate, acetic acid, or a mixed solvent of two or more thereof] in hydrogen atmosphere at atmospheric pressure or under pressure or in the presence of ammonium formate, at a temperature of 0 to 200° C.

Pharmacological Activity:

It was confirmed by the method described in WO 01/40227 that the crystals of a non-solvate of (3R)-1-butyl-2,5-dioxo-3-[(1R)-1-hydroxy-1-cyclohexylmethyl]-9-[4-(4-carboxyphenyloxy)phenylmethyl]-1,4,9-triazaspiro [5.5]undecane hydrochloride or the solvates thereof in solid have an antagonistic activity against the interaction between chemokine and a chemokine receptor, at almost the same level as that of the amorphous substance produced by the method described in the specification of WO 02/074770.

Toxicity:

The toxicity of the inventive compound is so low that the inventive compound when dosed at 2000 mg/kg in a single dosing test using rats never showed distinct toxicity. Thus, the inventive compound is determined as sufficiently safe for medical use.

INDUSTRIAL APPLICABILITY

Application to Pharmaceuticals:

The inventive compound regulate the effect of chemokine/chemokine receptor in animal included human, especially human, so they are used for prevention and/or treatment of various inflammatory diseases, asthma, atopic dermatitis, nettle rash, allergic diseases (allergic bronchopulmonary aspergillosis, allergic eosinophilic gastroenteritis and the like), nephritis, nephropathy, hepatitis, arthritis, chronic rheumatoid arthritis, psoriasis, rhinitis, conjunctivitis, ischemia-reperfusion injury, multiple sclerosis, ulcerative colitis, acute respiratory distress syndrome, shock accompanied by bacterial infection, diabetes mellitus, autoimmune diseases, graft versus host disease, immunosuppression, metastasis, acquired immunodeficiency syndrome and the like.

For the purpose above described, the inventive compound, salts thereof, acid addition salts or hydrates thereof may be normally administered systemically or locally, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered for example, in the form of solid for oral administration, liquid forms for oral administration, injections, liniments or suppositories for parenteral administration.

Solid forms for oral administration include compressed tablets, pills, capsules, dispersible powders, and granules. Capsules include hard capsules and soft capsules.

In such solid forms, one or more of the active compound(s) may be admixed with vehicles (such as lactose, mannitol, glucose, microciystalline cellulose or starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more layers. And further, coating may include containment within capsules of absorbable materials such as gelatin.

Liquid forms for oral administration include pharmaceutically acceptable solutions, suspensions, emulsions, syrups and elixirs. In such forms, one or more of the active compound(s) may be dissolved, suspended or emulsified into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvent(s) for injection immediately before use. In injections, one or more of the active compound(s) may be dissolved, suspended or emulsified into solvent(s). The solvents may include distilled water for injection, saline, vegetable oil, propylene glycol, polyethylene glycol, alcohol, e.g. ethanol, or a mixture thereof. Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared and compensated according to sterile methods. They may also be manufactured in the form of sterile solid forms such as freeze-dried products, which may be dissolved in sterile water or some other sterile diluent(s) for injection immediately before use.

Other forms for parenteral administration include liquids for external use, ointments and endermic liniments, inhalations, sprays, suppositories and pessaries for vaginal administration which comprise one or more of the active compound(s) and may be prepared by methods known per se.

Sprays may comprise additional substances other than diluents, such as stabilizing agents, such as sodium sulfate, isotonic buffers, such as sodium chloride, sodium citrate or citric acid. For preparation of such sprays, for example, the method described in the U.S. Pat. No. 2,868,691 or 3,095,355 may be used.

The compound of the present invention may be used together with at least one member of other preventive and/or treating agent(s) for HIV infection (particularly an agent for preventive and/or treating agent AIDS). In that case, the drug as such may be mixed with pharmacologically acceptable excipient, binder, disintegrating agent, lubricant, stabilizer, solubilizer, diluent, etc. either separately or simultaneously to make into a pharmaceutical preparation and that can be administered either orally or parenterally as a pharmaceutical composition for prevention and/or treatment of HIV infection.

The compound of the present invention has an infection inhibiting activity to HIV-I which acquired resistance to other agent for preventive and/or treating HIV infection (particularly, an agent for preventive and/or treating agent AIDS). Therefore, it is also able to be used for HIV-infected patients to whom other agent for preventive and/or treating HIV infection is no longer effective. In that case, although the compound of the present invention may be used solely, it may be also used together with an agent for preventive and/or treating HIV infection where infected HIV-1 strain acquired resistance or with other drugs.

The present invention covers the case where the compound of the present invention is combined with a drug which does not inhibit the HIV infection whereby preventive and/or treating effect for HIV infection is enhanced as compared with a single preparation.

Examples of other agent for preventive and/or treating HIV infection used for a combination with the compound of the present invention are reverse transcriptase inhibitor, protease inhibitor, chemokine antagonist (such as CCR2 antagonist, CCR3 antagonist, CCR4 antagonist, CCR5 antagonist and CXCR4 antagonist), fusion inhibitor, antibody to surface antigen of HIV-1 and vaccine of HIV-1.

Reverse transcriptase inhibitors are concretely (1) nucleoside/nucleotide reverse transcriptase inhibitors: zidovudine (brand name: Retrovir), didanosine (brand name: Videx), zalcitabine (brand name: HIVID), stavudine (brand name: Zerit), lamivudine (brand name: Epivir), abacavir (brand name: Ziagen), adefovir, adefovir dipivoxil, emtricitabine (brand name: Coviracil) or PMPA (brand name: Tenofovir) etc. and (2) normucleoside reverse transcriptase inhibitors: nevirapine (brand name: Viramune), delavirdine (brand name: Rescriptor), efavirenz (brand name: Sustiva, Stocklin) or capravirine (AG1549) etc.

Protease inhibitors are concretely indinavir (brand name: Crixivan), ritonavir (brand name: Norvir), nelfinavir (brand name: Viracept), saquinavir (brand name: Invirase, Fortovase), amprenavir (brand name: Agenerase), lopinavir (brand name: Kaletra) or tipranavir etc.

As chemokine antagonists, internal ligand of chemokine receptor, its derivatives, its non-peptide low molecular compound or antibody of chemokine receptor are included.

The examples of internal ligand of chemokine receptor are concretely, MIP-1α, MIP-1β, RANTES, SDF-1α, SDF-1β, MCP-1, MCP-2, MCP-4, Eotaxin and MDC etc.

The derivatives of internal ligand are concretely, AOP-RANTES, Met-SDF-1α, Met-SDF-1β etc.

Antibodies of chemokine receptor are concretely, Pro-140 etc.

CCR2 antagonists are concretely written in specification of WO99/07351, WO99/40913, WO00/46195, WO00/46196, WO00/46197, WO00/46198, WO00/46199, WO00/69432 or WO00/69815 or in *Bioorg. Med. Chem. Lett.*, 10, 1803 (2000) etc.

CCR3 antagonists are concretely written in specification of DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/

53172, WO00/53600, WO00/58305, WO00/59497, WO00/59498, WO00/59502, WO00/59503, WO00/62814, WO00/73327 or WO01/09088 etc.

CCR5 antagonists are concretely written in specification of WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000309598, WO00/51607, WO00/51608, WO00/51609, WO00/51610, WO00/56729, WO00/59497, WO00/59498, WO00/59502, WO00/59503, WO00/76933, WO98/25605 or WO99/04794, WO99/38514 or in *Bioorg. Med. Chem. Lett.*, 10, 1803 (2000) etc.

CXCR4 antagonists are concretely, AMD-3100, T-22, KRH-1120 or the compounds written in specification of WO00/66112 etc.

Fusion Inhibitors are concretely, T-20 (Pentafuside) and T-1249 etc.

The examples of combination agents written above are intended to illustrate the present invention, but do not limit them.

The typical examples of the usual dosage in clinical trials of reverse transcriptase inhibitors or protease inhibitors written below are intended to illustrate the present invention, but do not limit them.

Zidovudine: 100 mg capsule, 200 mg per dose, 3 times per day;
300 mg tablet, 300 mg per dose, twice per day;
didanosine: 25-200 mg tablet, 125-200 mg per dose, twice per day;
zalcitabine: 0.375-0.75 mg tablet, 0.75 mg per dose, 3 times per day;
stavudine: 15-40 mg capsule, 30-40 mg per dose, twice per day;
lamivudine: 150 mg tablet, 150 mg per dose, twice per day;
abacavir: 300 mg tablet, 300 mg per dose, twice per day;
nevirapine: 200 mg tablet, 200 mg per dose, once per day for 14 days and then twice per day;
delavirdine: 100 mg tablet, 400 mg per dose, 3 times per day;
efavirenz: 50-200 mg capsule, 600 mg per dose, once per day;
indinavir: 200-400 mg capsule, 800 mg per dose, 3 times per day;
ritonavir: 100 mg capsule, 600 mg per dose, twice per day;
nelfinavir: 250 mg tablet, 750 mg per dose, 3 times per day;
saquinavir: 200 mg capsule, 1,200 mg per dose, 3 times per day;
amprenavir: 50-150 mg tablet, 1,200 mg per dose, twice per day.

BEST MODE FOR CARRYING OUT THE INVENTION

Figure 1:
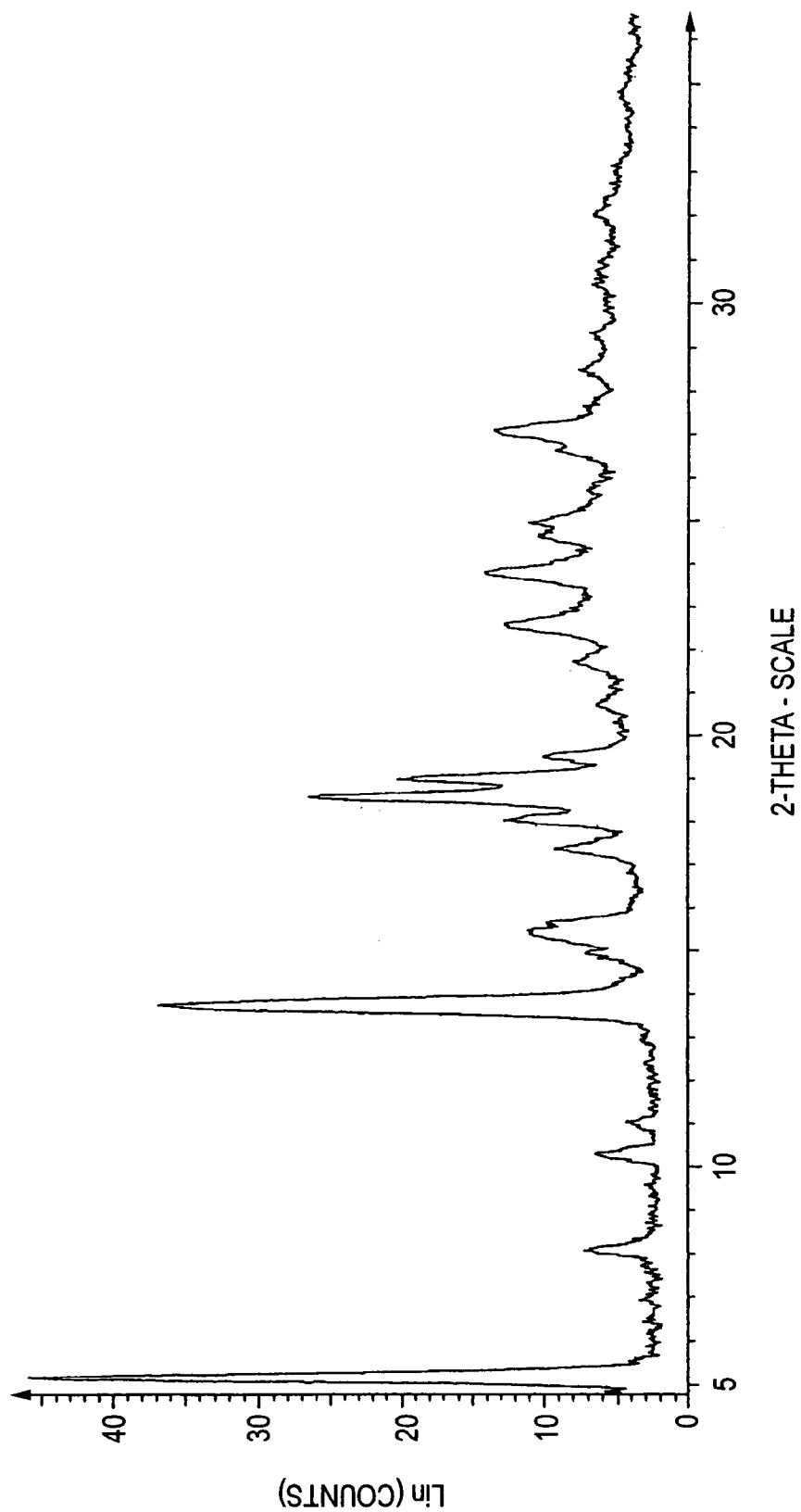
FIG. 1 shows the powdery X ray diffraction spectrum data of Crystal A obtained in Example 1.

The invention is now described in detail below in Reference Examples and Examples. However, the present invention is not limited thereto.

REFERENCE EXAMPLE 1

(3R)-1-Butyl-2,5-dioxo-3-[(1R)-1-hydroxy-1-cyclohexylmethyl]-9-benzyl-1,4,9-triazaspiro[5.5]undecane methanesulfonate n-Butylamine (310 g), (2R,3R)-2-(t-butoxycarbonylamino)-3-cyclohexyl-3-hydroxypropionic acid (1,200 g), and 2-morpholinoethylisocyanide (600 g) were sequentially added to a solution of 1-benzyl-4-piperidone (798 g) in methanol (4 L) in nitrogen atmosphere. The resulting reaction mixture was agitated at 50 to 55° C. for 3 hours. The reaction mixture was cooled to room temperature, and concentrated hydrochloric acid (2 L) was added thereto. The reaction mixture was agitated at 50 to 55° C. for 2 hours. The reaction mixture was cooled to room temperature, methanol (2 L) and water (12 L) were added thereto, and then a 25% aqueous sodium hydroxide solution (3.03 L) was added thereto. The reaction mixture was concentrated and extracted in ethyl acetate. To the extract solution, glacial acetic acid (1.14 L) was added, for refluxing for 2 hours. The reaction mixture was cooled to room temperature, rinsed sequentially with water, a 2-M aqueous sodium hydroxide solution (9.5 L) and 33% aqueous sodium chloride (5.4 L) and then concentrated. To the resulting residue, ethyl acetate (10.4 L) was added. The resulting mixture was agitated at 60 to 65° C. for 30 minutes, and methanesulfonic acid (388 g) was added thereto at 60 to 70° C. The reaction mixture was agitated at the same temperature for 10 minutes to precipitated the crystals. The reaction mixture was cooled first to 40 to 45° C. and then to 0 to 5° C., followed by agitation for 1 hour. The precipitated crystals were filtered, washed with ethyl acetate and dried to obtain the entitled compound (1,802 g) with the following physicochemical properties.

TLC: Rf; 0.42 (chloroform:methanol=10:1) NMR(200 MHz, CD$_3$OD). δ 7.51-7.22 (m, 5H), 4.36 (s, 2H), 4.14 (d, J=2.2 Hz, 1H), 4.00 (m, 1H), 3.76 (m, 1H), 3.59-3.38 (m, 3H), 3.30-3.03 (m, 2H), 2.70 (s, 3H), 2.54-1.83 (m, 6H), 1.82-1.56 (m, 5H), 1.53-1.08 (m, 6H), 1.06-0.77 (m, 5H).

REFERENCE EXAMPLE 2

(3R)-1-Butyl-2,5-dioxo-3-[(1R)-1-hydroxy-1-cyclohexylmethyl]-1,4,9-triazaspiro[5.5]undecane methanesulfonate In nitrogen atmosphere, 10% palladium/carbon (18 g) was added to a solution (3.3 L) of the compound (1,792 g) produced in Reference Example 1 in dimethylformamide. The reaction mixture was purged with hydrogen gas. The reaction mixture was agitated at a hydrogen pressure of 0.5 MPa at 80° C. for 1 hour. The reaction mixture was cooled to room temperature and filtered to obtain a solution of the entitled compound in dimethylformamide.

REFERENCE EXAMPLE 3

(3R)-1-Butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane Triethylamine (340 g), sodium triacetoxyborohydride (1,486 g) and 4-(4-formylphenyloxy)benzoic acid (969 g) were added to a solution (8.4 L) of the compound produced in Reference Example 2 in dimethylformamide in nitrogen atmosphere. The reaction mixture was agitated at room temperature for 8 hours. The reaction mixture was heated to 65 to 70° C., and water (3.3 L) heated to 70° C. was added thereto. Then, the resulting mixture was agitated at 65 to 70° C. for 10 minutes to precipitate the crystals. Furthermore, water (3.3 L) heated to 70° C. was added to the reaction mixture, followed by agitation at 65 to 70° C. for 10 minutes. The reaction mixture was cooled down to 15 to 30° C. and agitated for 30 minutes. The precipitated crystals were filtered and washed with aqueous 60% methanol solution to obtain the entitled compound (2354 g) with the following physicochemical properties.

TLC: Rf; 0.48 (chloroform:methanol: acetic acid=20:4:1) NMR (300 MHz, d$_6$-DMSO): δ 7.92 (d, J=8.7 Hz, 2H), 7.67 (m, 1H), 7.37 (d, J=8.4 Hz, 2H), 7.06 (d, J=8.4 Hz, 2H), 7.01 (d, J=8.7 Hz, 2H), 5.07 (br-s, 1H), 3.95 (s, 1H), 3.51 (s, 2H), 3.40-3.09 (m, 3H), 2.83-2.62 (m, 4H), 2.10-1.84 (m, 4H), 1.80-1.44 (m, 7H), 1.40-1.22 (m, 3H), 1.20-1.04 (m, 3H), 0.87 (t, J=7.0 Hz, 3H), 0.85-0.75 (m, 2H).

EXAMPLE 1

Crystals of a Non-Solvate of (3R)-1-butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane Hydrochloride (Crystal A)

The compound (wet weight of 30.3 kg, equivalent dry weight of 20 kg, containing a mixed solvent (10.3 kg) of methanol:water (=6:4)) produced in Reference Example 3 was added to a solution of 0.032 M hydrochloric acid (50.8 L) in methanol (126 L) at 20 to 50° C. The reaction mixture was agitated at 50 to 55° C. for 30 minutes. The reaction mixture was filtered and washed with an 70% aqueous methanol solution. The filtrate was agitated at 50 to 55° C. The reaction mixture solution was cooled down to room temperature and agitated for 10 minutes. Furthermore, the reaction mixture was cooled down to 0 to 5° C., to precipitate the crystals. Methanol (41 L) was added to the thus obtained suspension and was then agitated at 0 to 5° C. for 1 hour, followed by addition of water (58 L) cooled to 5° C. The resulting mixture was agitated at the same temperature for 30 minutes. The thus precipitated crystals were filtered, washed in a 60% aqueous methanol solution and dried to obtain Crystal A (18.5 kg) with the following physicochemical properties as the inventive compound. Additionally, the crystals had a mean particle size of 15.8 μm (measured by Laser Diffraction Particle Size Analyzer SALD-2100, SHIMADZU) and a melting point of about 235° C. (measured by the method using capillary described in Japanese Pharmacopoeia).

Figure 2:
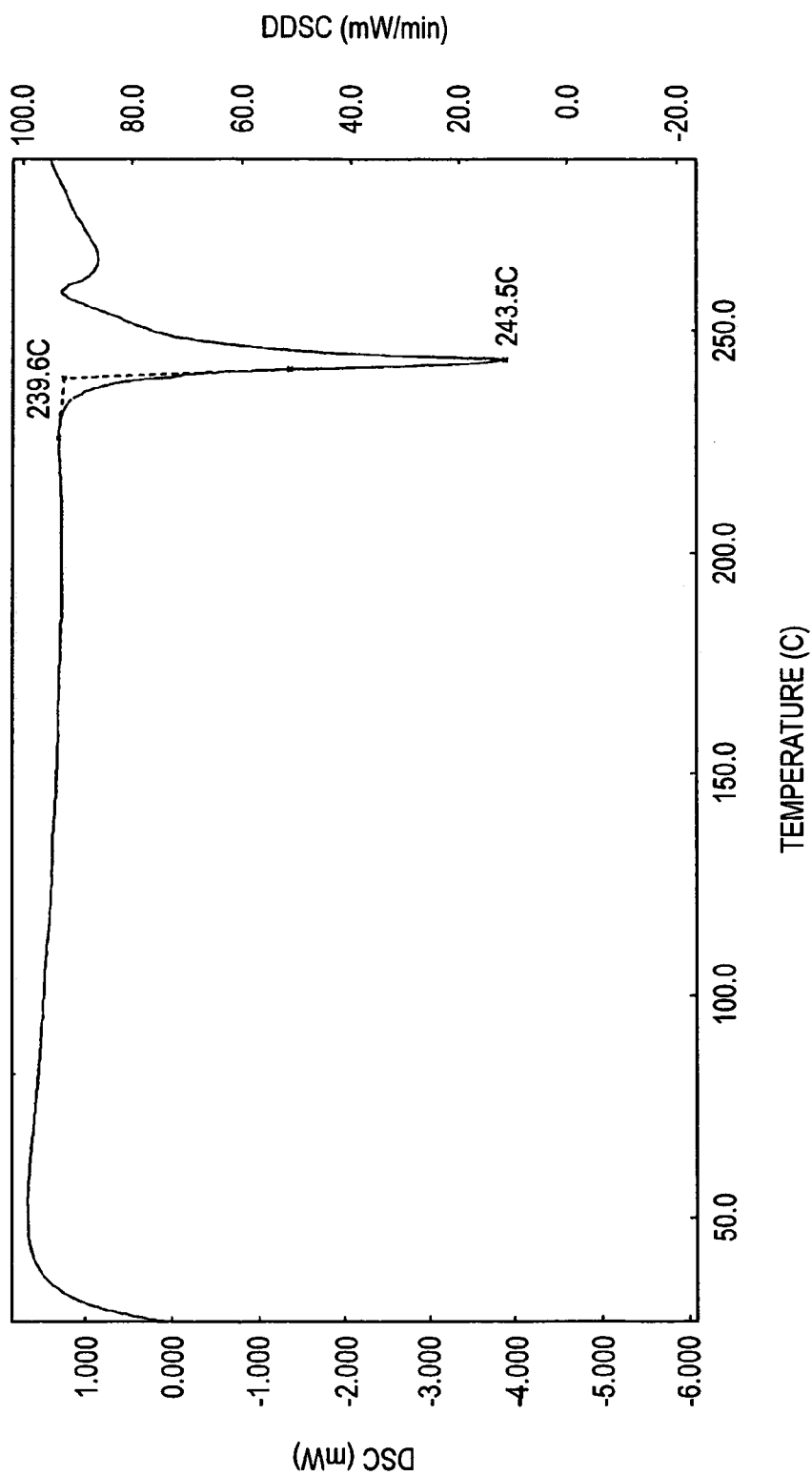
FIG. 2 shows the differential scanning calorimetric (DSC) data of Crystal A obtained in Example 1.
Figure 3:
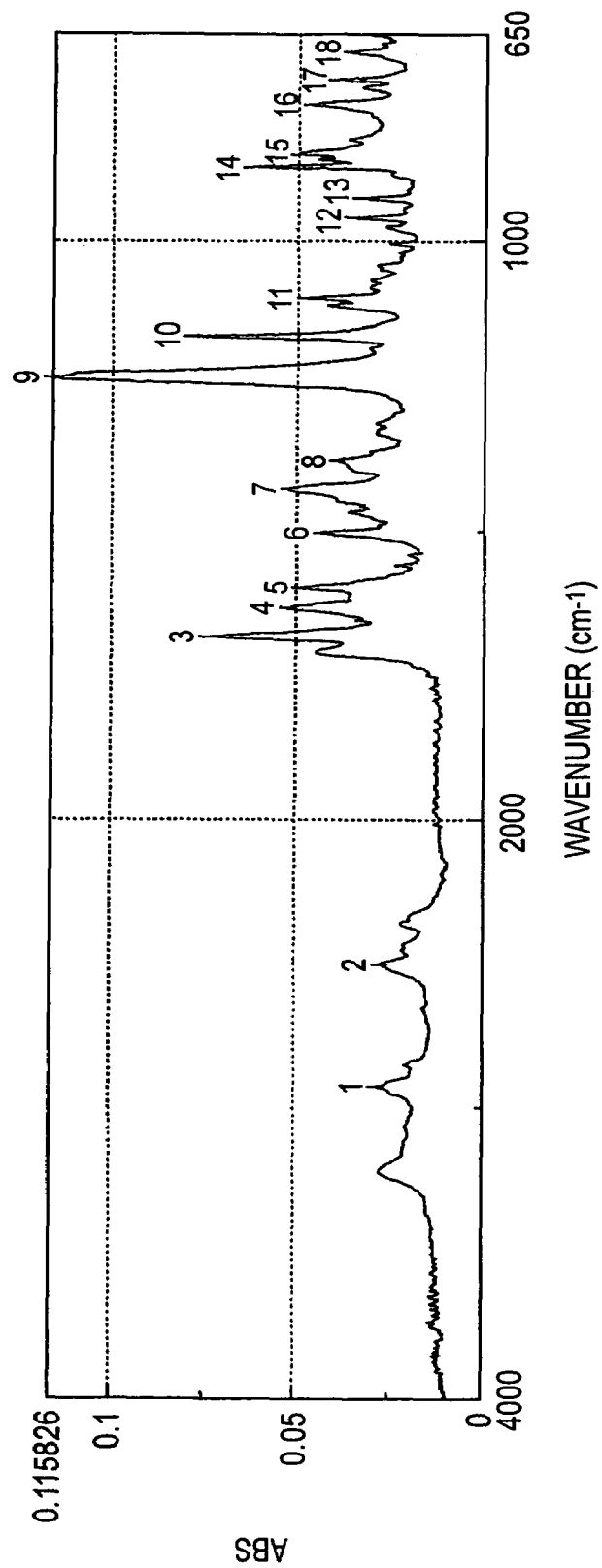
FIG. 3 shows the IR absorption spectrum data of Crystal A obtained in Example 1.
Figure 4:
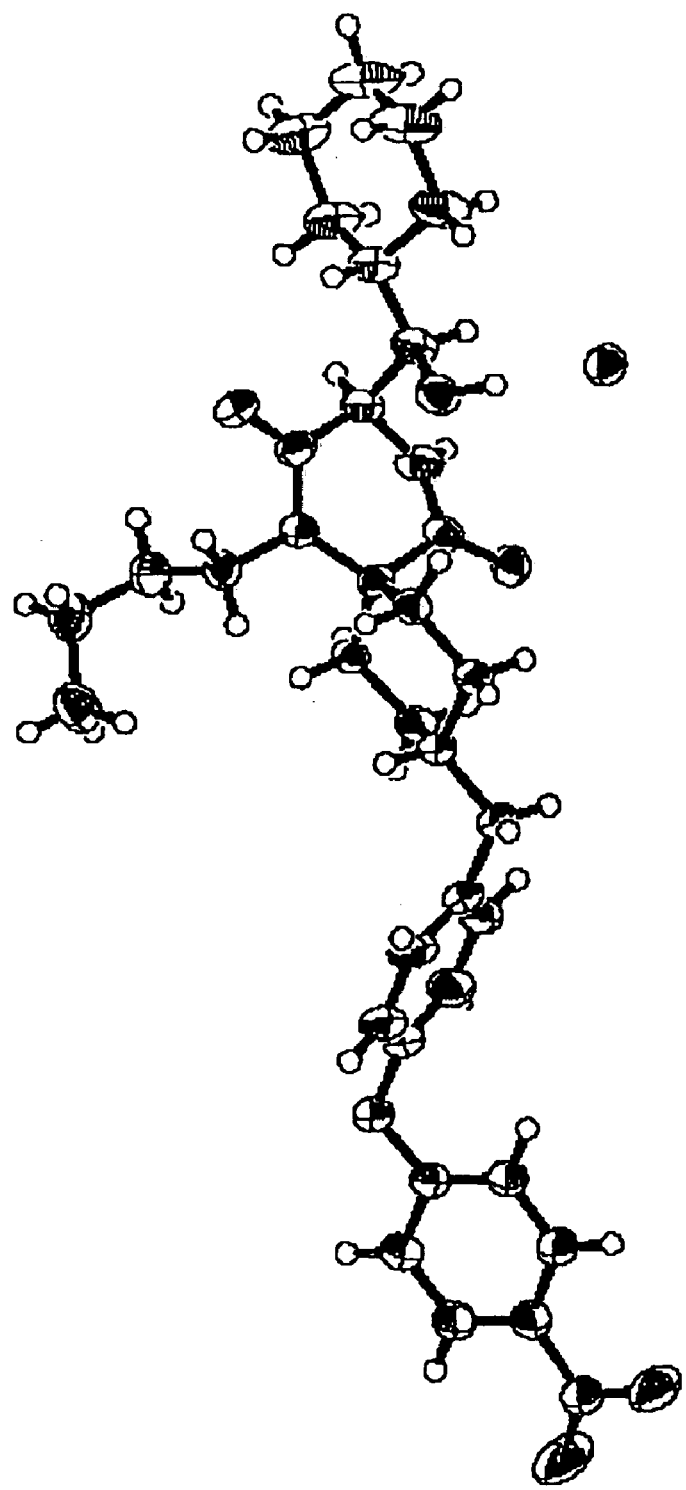
FIG. 4 shows the structural analysis data (1) of Crystal A obtained in Example 1 by single crystal X ray diffractometry.
Figure 5:
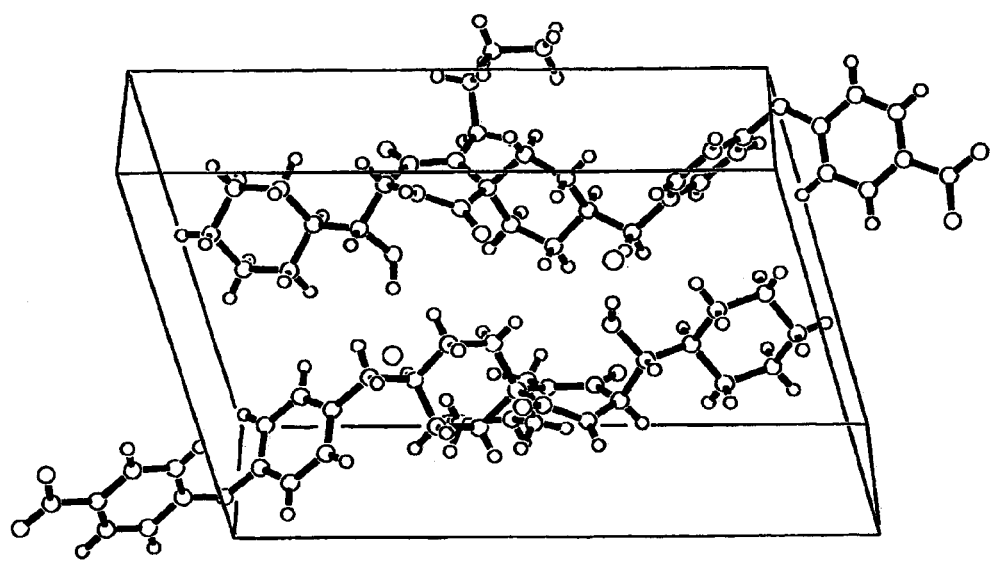
FIG. 5 shows the structural analysis data (2) of Crystal A obtained in Example 1 by single crystal X ray diffractometry.

FIG. 1 shows the powdery X ray diffraction spectrum data of Crystal A as the thus obtained inventive compound; FIG. 2 shows the differential scanning calorimetric data thereof; FIG. 3 shows the IR absorption spectrum data thereof; and FIGS. 4 and 5 show the structural analysis data thereof by single crystal X ray diffractometry.

(1) Data for Powdery X Ray Diffractometry

Measuring Conditions:
  Apparatus: BRUI<ER DISCOVER with GADDS (C2)
  Target: Cu
  Filter: no filter
  Voltage: 40 kV
  Current: 40 mA
  Exposure time: 180 sec Results:

The results are shown in Table 2.

TABLE 2

| diffraction angle (2θ) | half-value width | relative intensity |
|---|---|---|
| 5.15 | 0.22 | High |
| 8.06 | 0.22 | Moderate |
| 10.26 | 0.26 | Moderate |
| 11.01 | 0.23 | Moderate |
| 13.72 | 0.39 | High |
| 15.46 | 0.74 | Moderate |
| 17.36 | 0.24 | Moderate |
| 18.03 | 0.22 | Moderate |
| 18.58 | 0.23 | Slightly high |
| 19.00 | 0.21 | Slightly high |
| 19.51 | 0.20 | Moderate |
| 20.71 | 0.19 | Moderate |
| 21.73 | 0.25 | Moderate |
| 22.58 | 0.36 | Moderate |
| 23.80 | 0.34 | Moderate |
| 24.96 | 0.61 | Moderate |
| 27.07 | 0.45 | Moderate |

(2) Data for Differential Scanning Calorimetry

Measuring Conditions:
  Apparatus: SEIKO INSTRUMENT DSC6200
  Sample weight: 2.8 mg
  Sample cell: SUS sealed container
  Nitrogen gas flow: 20 mL/min
  Temperature elevation rate: 10° C./min Results:
  Consequently, it was shown that Crystal A had an endothermic peak around 244° C.

(3) Data for IR Absorptiometry

Measuring Conditions:
  Apparatus: FTIR-660 plus/SensIR DuraScope manufactured by JASCO CORPORATION
  Resolution: 4 $cm^{-1}$
  Number of scanning: 16 times Results:
  IR (Attenuated total reflectance method (hereinafter referred to as "ATR method"): 2924, 2504, 1682, 1632, 1597, 1503, 1426, 1377, 1235, 1163, 1098, 961, 928, 876, 855, 770, 727, 681 $cm^{-1}$ (4) Data for Structural Analysis by Single Crystal X Ray Diffractometry Measuring Conditions:
  Apparatus: RIGAKU RAXIS-RAPID imaging plate
  Target: CuKα (λ=1.54178 Å)
  Filter: graphite monochromated
  Voltage: 60 kV
  Current: 90 mA
  Scanning speed: 1°/min Results:
  The crystallographic data were shown below.
  Lattice constant:
    a=11.8105 (4) Å
    b=7.8730 (2) Å
    c=18.2351 (7) Å
  Space group: $P2_1$ (#4)
  R factor: 0.042

EXAMPLE 2

Solvate of (3R)-1-butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane Hydrochloride with Methanol and Water in Solid (Solid B)

The compound (dry weight of 28.4 g) produced in Reference Example 3 was added to a solution of 0.35 M hydrochloric acid (170 mL) in methanol (256 mL). The reaction mixture was dissolved at 50 to 55° C. The reaction mixture was cooled down to 20 to 30° C. and was agitated for 30 minutes. Furthermore, the reaction mixture was cooled down to 0 to 5° C. and agitated for 1 hour. The precipitated solid was filtered and recovered, and then dried to obtain Solid B (27.1 g) with the following physicochemical properties.

It was confirmed by NMR that Solid B was the solvate with methanol and water.

Figure 6:
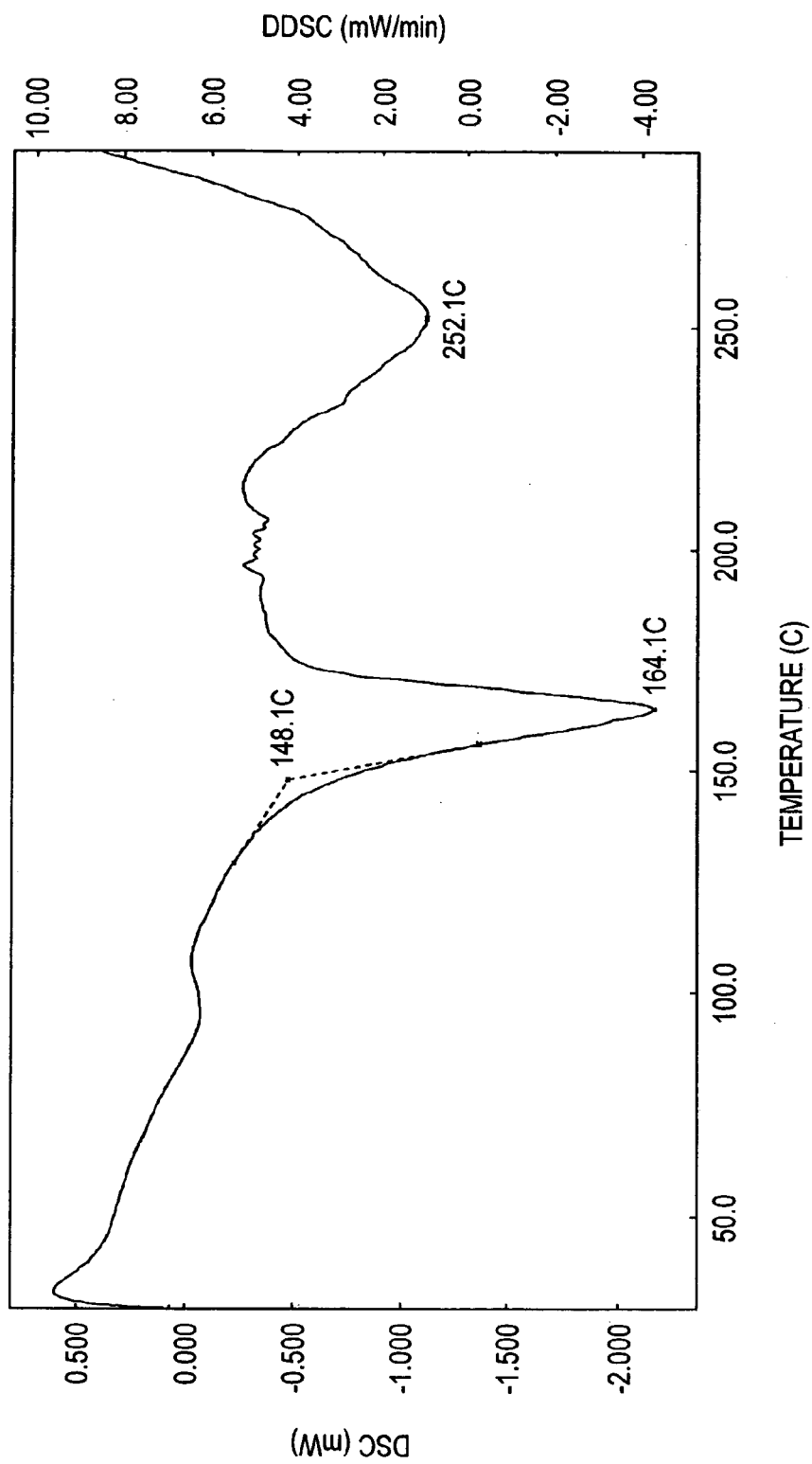
FIG. 6 shows the differential scanning calorimetric (DSC) data of Solid B obtained in Example 2.
Figure 7:
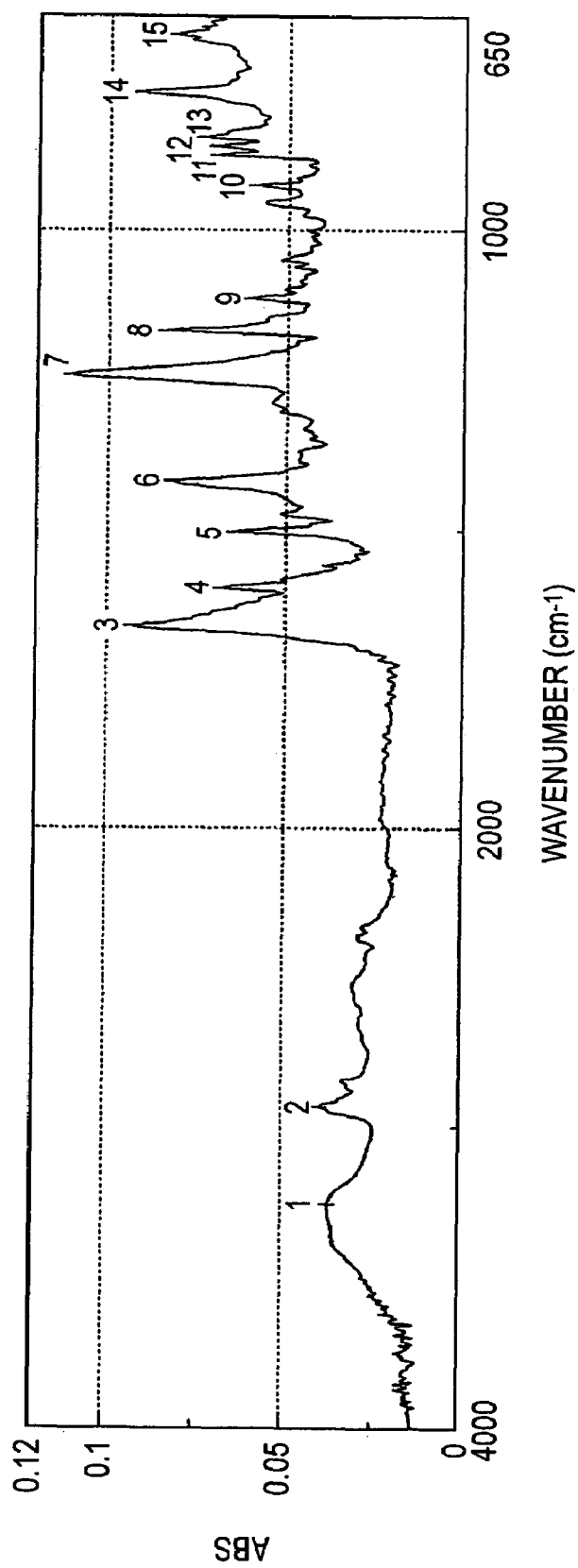
FIG. 7 shows the IR absorption spectrum data of Solid B obtained in Example 2.

FIG. 6 shows the differential scanning calorimetric data of Solid B and FIG. 7 shows the IR absorption spectrum data thereof.

(1) Data for Differential Scanning Calorimetry

Measuring Conditions:
  Apparatus: SEIKO INSTRUMENT DSC6200
  Sample weight: 3.4 mg
  Sample cell: SUS sealed container
  Nitrogen gas flow: 20 mL/min
  Temperature elevation rate: 10° C./min Results:
  Consequently, it was shown that Solid B had endothermic peaks around 164 and 252° C.

(2) Data for IR Absorptiometry

Measuring Conditions:
  Apparatus: FTIR-660 plus/SensIR DuraScope manufactured by JASCO CORPORATION
  Resolution: 4 $cm^{-1}$
  Number of scanning: 16 times Results:
  IR (ATR method): 3256, 2932, 1661, 1597, 1503, 1418, 1240, 1167, 1113, 928, 878, 862, 849, 775, 681 $cm^{-1}$

EXAMPLE 3

Solvate of (3R)-1-butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane hydrochloride with ethanol and/or water in solid (Solid C)

The compound (dry weight of 3.46 g) produced in Reference Example 3 was added to a solution of 6 M hydrochloric acid (1.05 mL) in ethanol (17.3 mL). The resulting mixture was dissolved under heating. Water (33.3 mL) heated to 50 to 53° C. was added to the reaction mixture and agitated for 21 hours. The reaction mixture was cooled down to room temperature, and then agitated for 30 minutes. Furthermore, the reaction mixture was cooled down to 0 to 5° C. and the precipitated crystals were filtered and dried to obtain Solid C (2.74 g) with the following physicochemical properties.

It was confirmed by NMR that Solid C was the solvate with ethanol and/or water.

Figure 8:
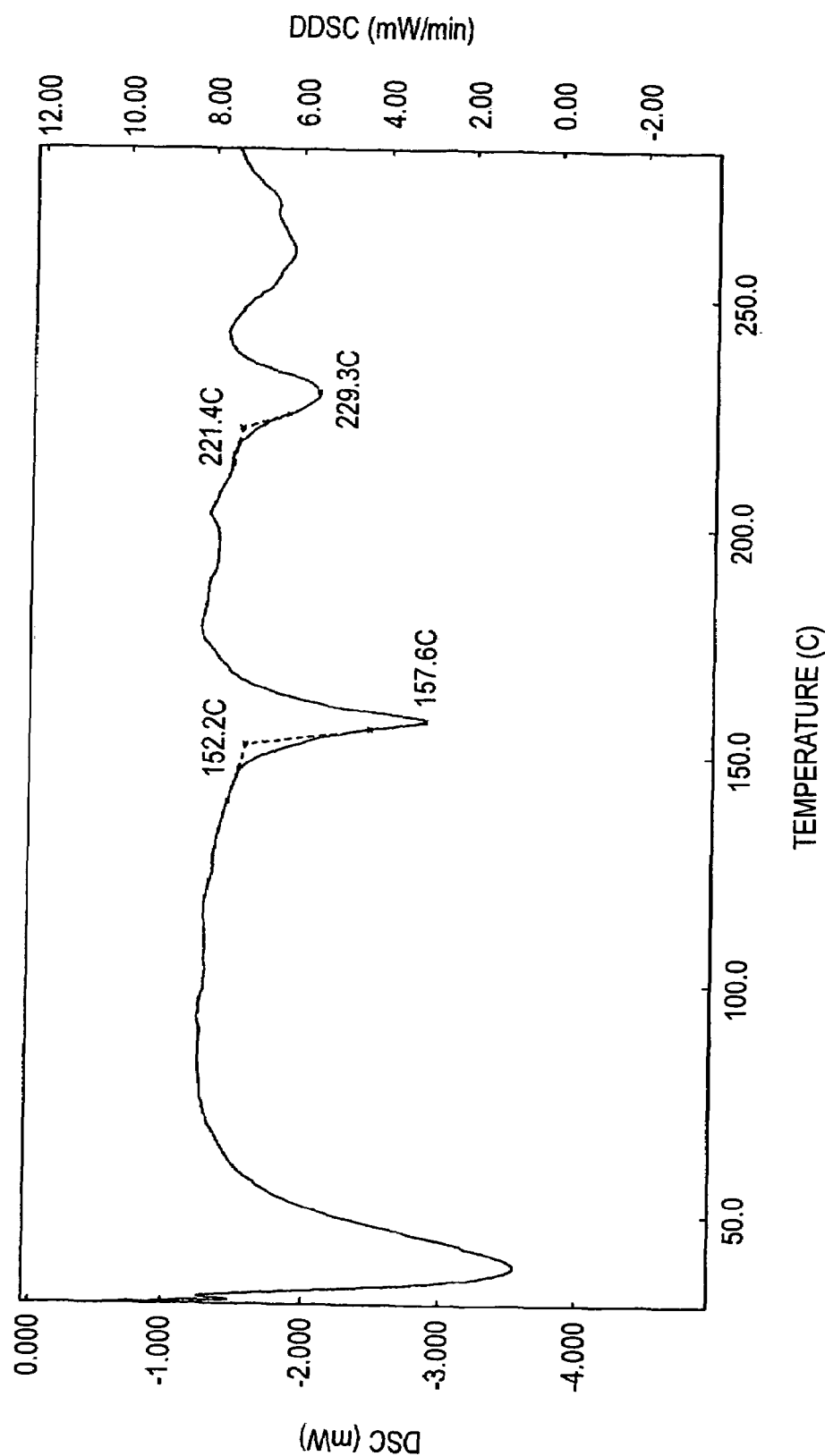
FIG. 8 shows the differential scanning calorimetric (DSC) data of Solid C obtained in Example 3.
Figure 9:
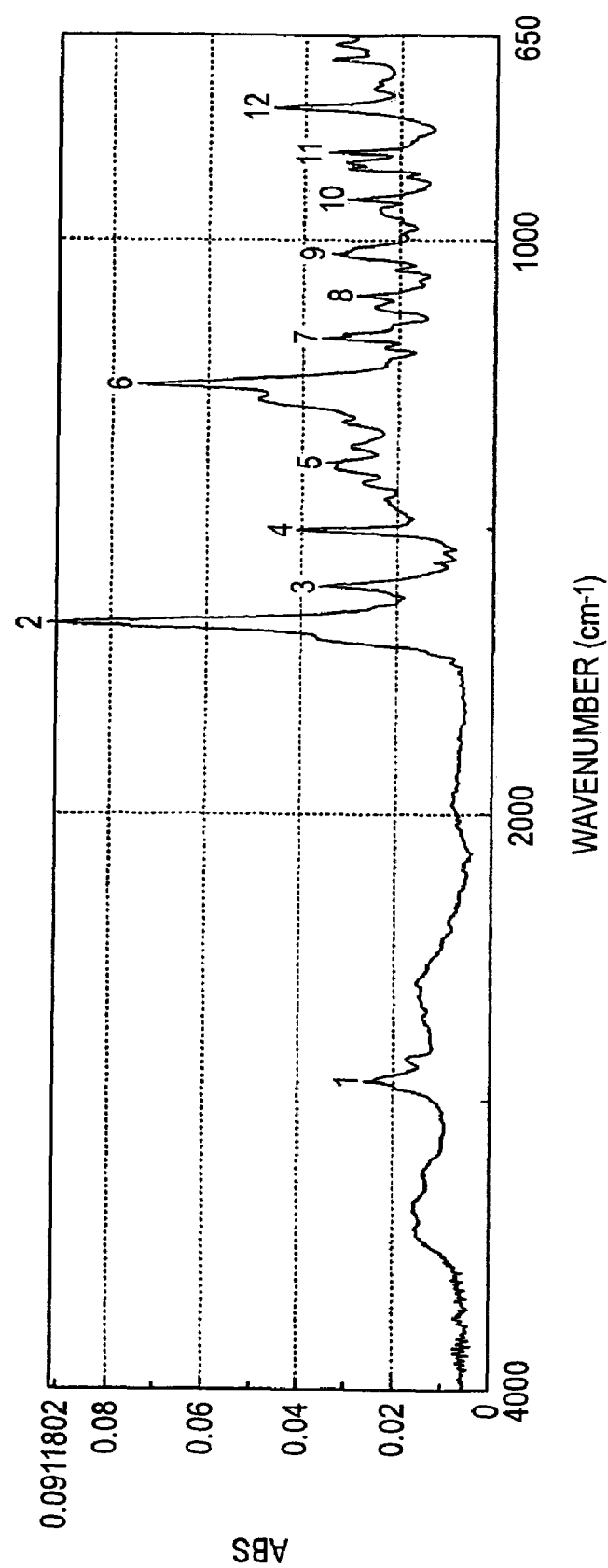
FIG. 9 shows the IR absorption spectrum data of Solid C obtained in Example 3.

FIG. 8 shows the differential scanning calorimetric data of Solid C and FIG. 9 shows the IR absorption spectrum data thereof.

(1) Data for Differential Scanning Calorimetry

Measuring Conditions:
  Apparatus: SEIKO INSTRUMENT DSC6200
  Sample weight: 2.05 mg
  Sample cell: SUS sealed container
  Nitrogen gas flow: 20 mL/min
  Temperature elevation rate: 10° C./min Results:
  Consequently, it was shown that Solid C had endothermic peaks around 158 and 229° C.

(2) Data for IR Absorptiometry

Measuring Conditions:
  Apparatus: FTIR-660 plus/SensIR DuraScope manufactured by JASCO CORPORATION
  Resolution: 4 $cm^{-1}$
  Number of scanning: 16 times Results:
  IR (ATR method): 2934, 1667, 1601, 1503, 1385, 1250, 1169, 1096, 1024, 930, 851, 775 $cm^{-1}$

EXAMPLE 4

Crystals of a non-solvate of (3R)-1-butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane Hydrochloride (Crystal A)

The solid (Solid B) (29.4 g) produced in Example 2 was added to ethyl acetate (440 mL). The reaction mixture was agitated at 60 to 65° C. for 1 hour. The reaction mixture was cooled down to room temperature and agitated for 30 minutes. Then, the precipitated crystals were filtered and dried to obtain Crystal A (28.5 g) with the same physicochemical properties as in Example 1, which was the inventive compound.

Figure 10:
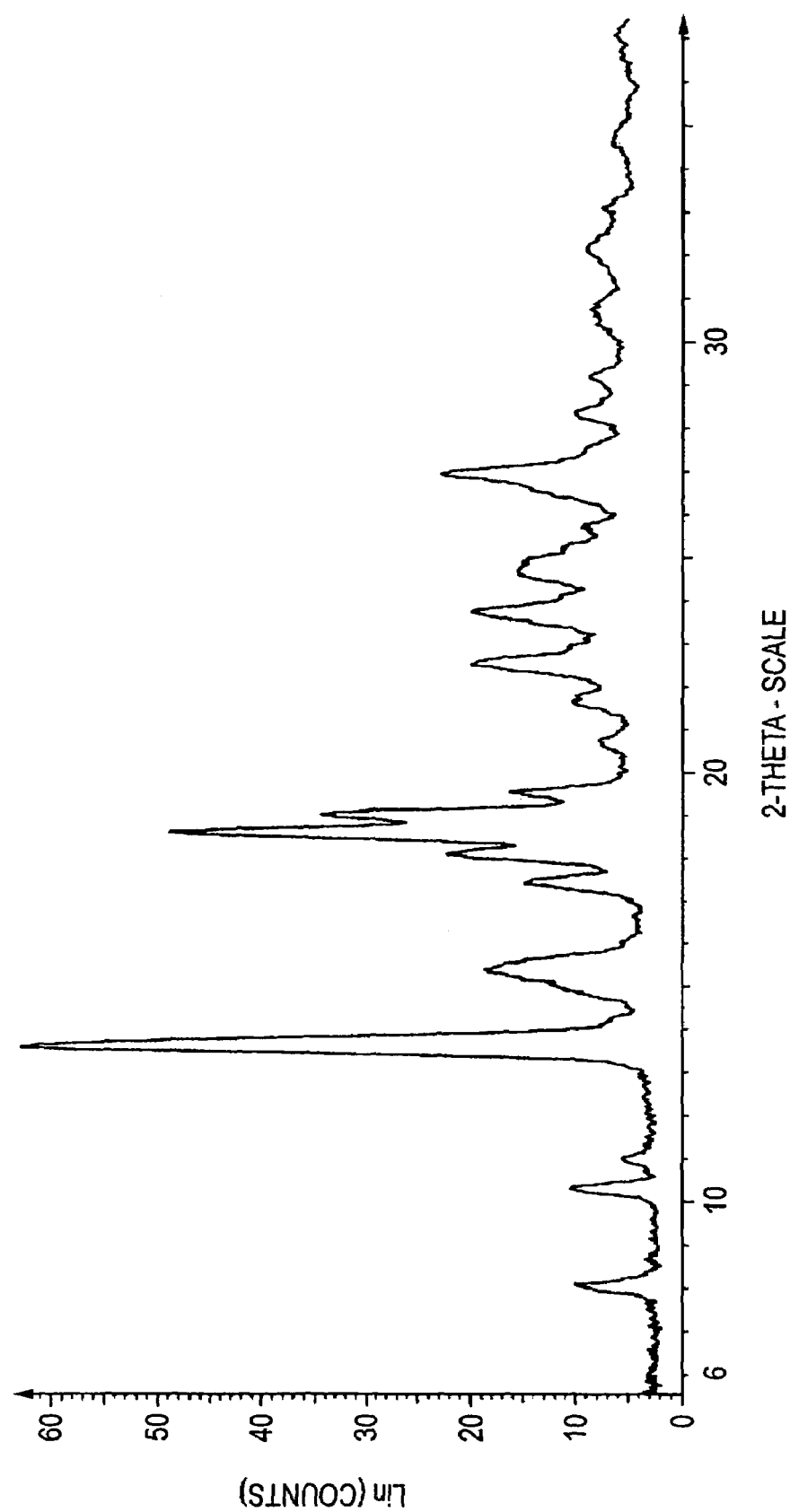
FIG. 10 shows the powdery X ray diffraction spectrum data of Crystal A obtained in Example 4.
Figure 11:
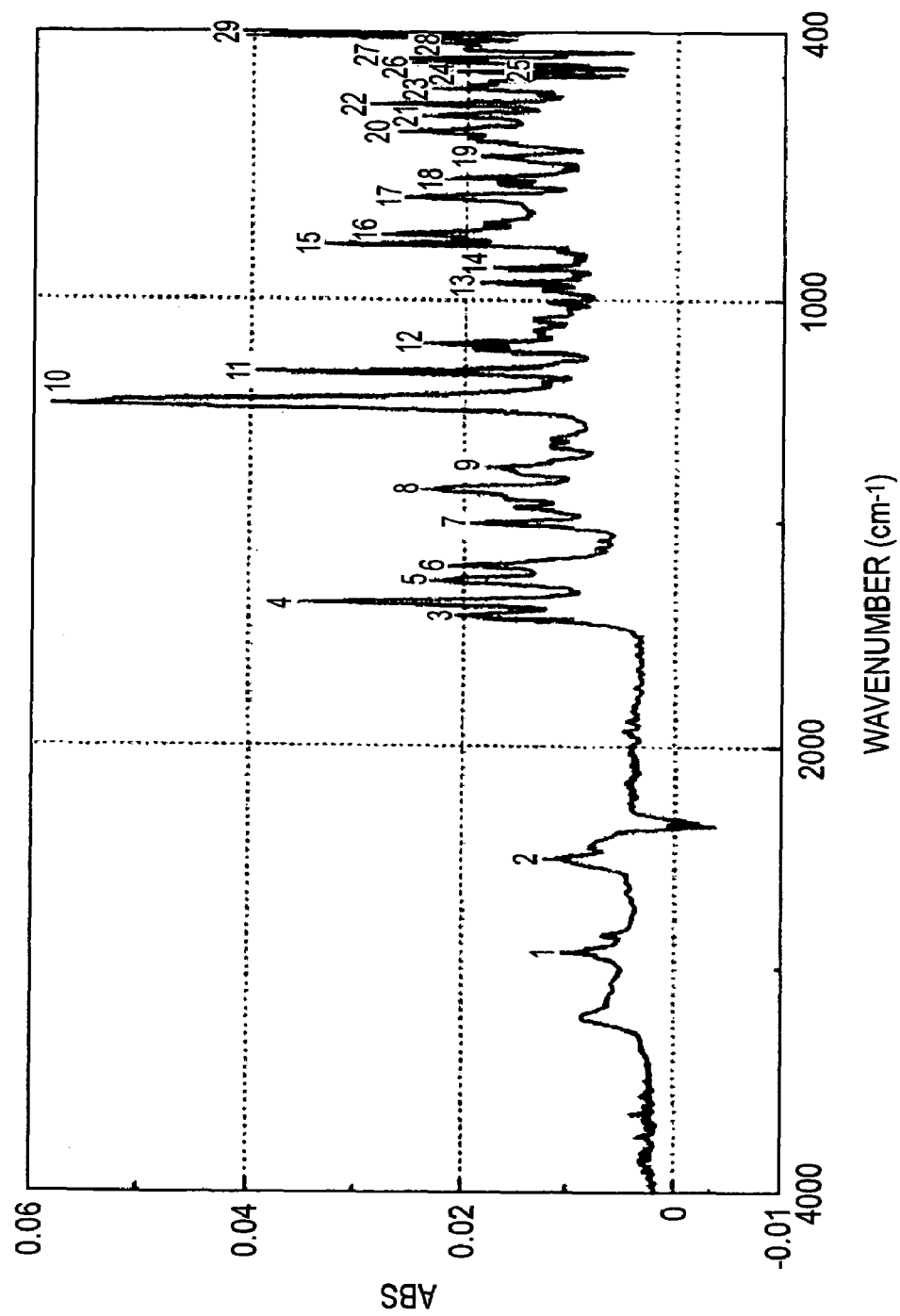
FIG. 11 shows the IR absorption spectrum data of Crystal A obtained in Example 4.

FIG. 10 shows the powdery X ray diffraction spectrum data of Crystal A produced in Example 4 and FIG. 11 shows the IR absorption spectrum data thereof.

COMPARATIVE EXAMPLE 1

Amorphous Substance of (3R)-1-butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane Hydrochloride (3R)-1-Butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane hydrochloride was produced by purification on a column with an eluent of chloroform: methanol (=5:1) according to the production process described in the specification of WO 02/074770.

Figure 12:
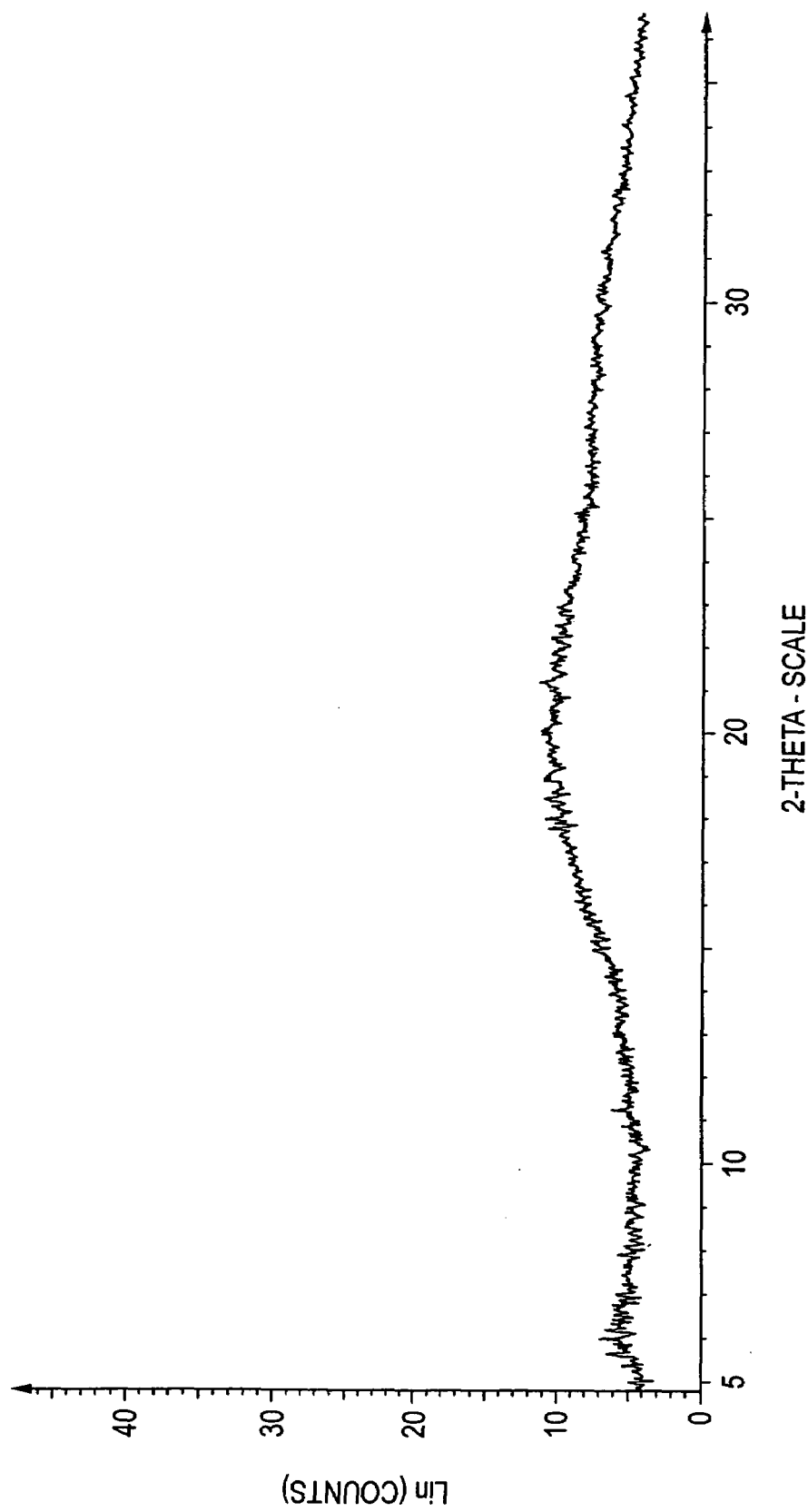
FIG. 12 shows the powdery X ray diffraction spectrum data of the amorphous obtained in Comparative Example 1.
Figure 13:
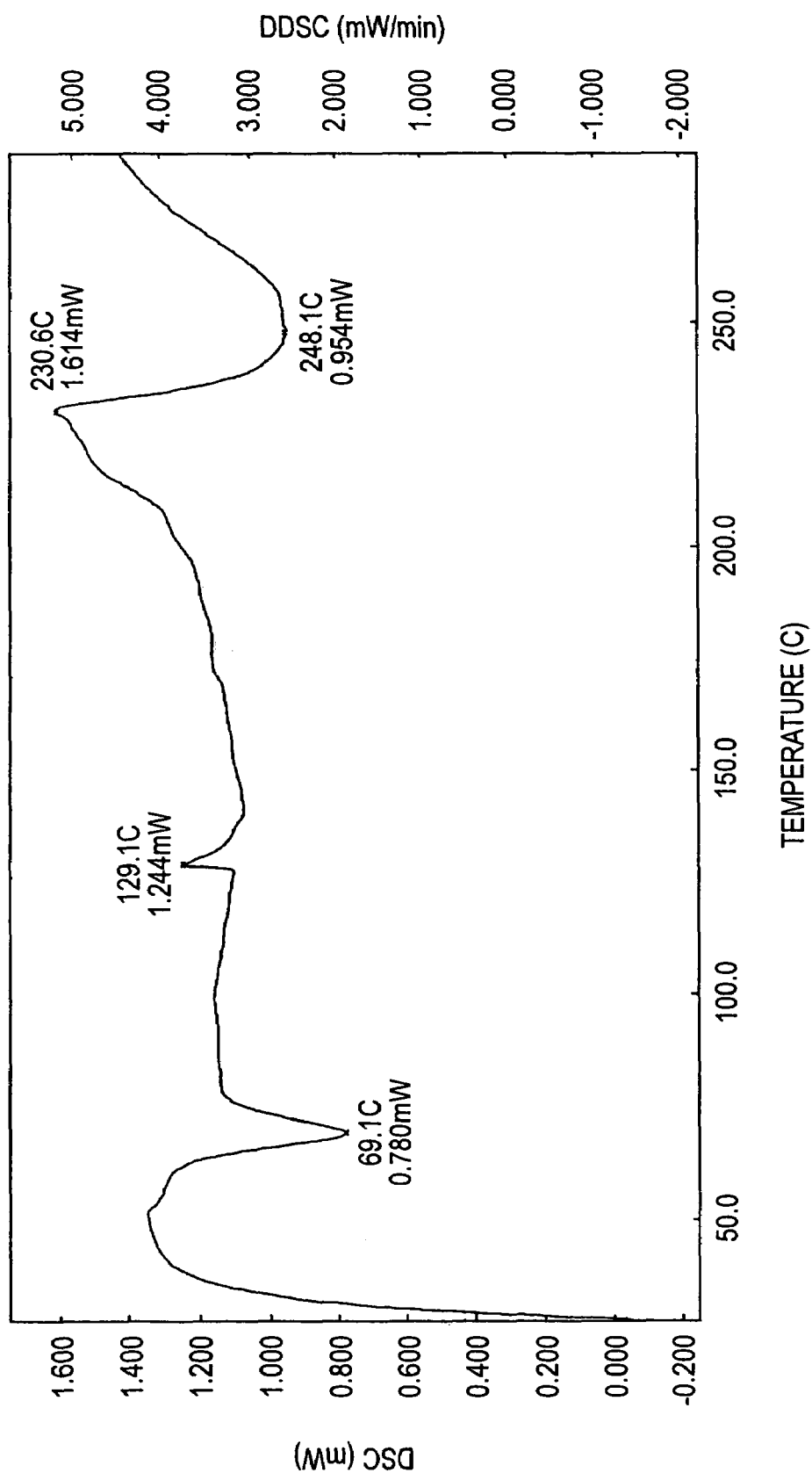
FIG. 13 shows the differential scanning calorimetric (DSC) data of the amorphous obtained in Comparative Example 1.
Figure 14:
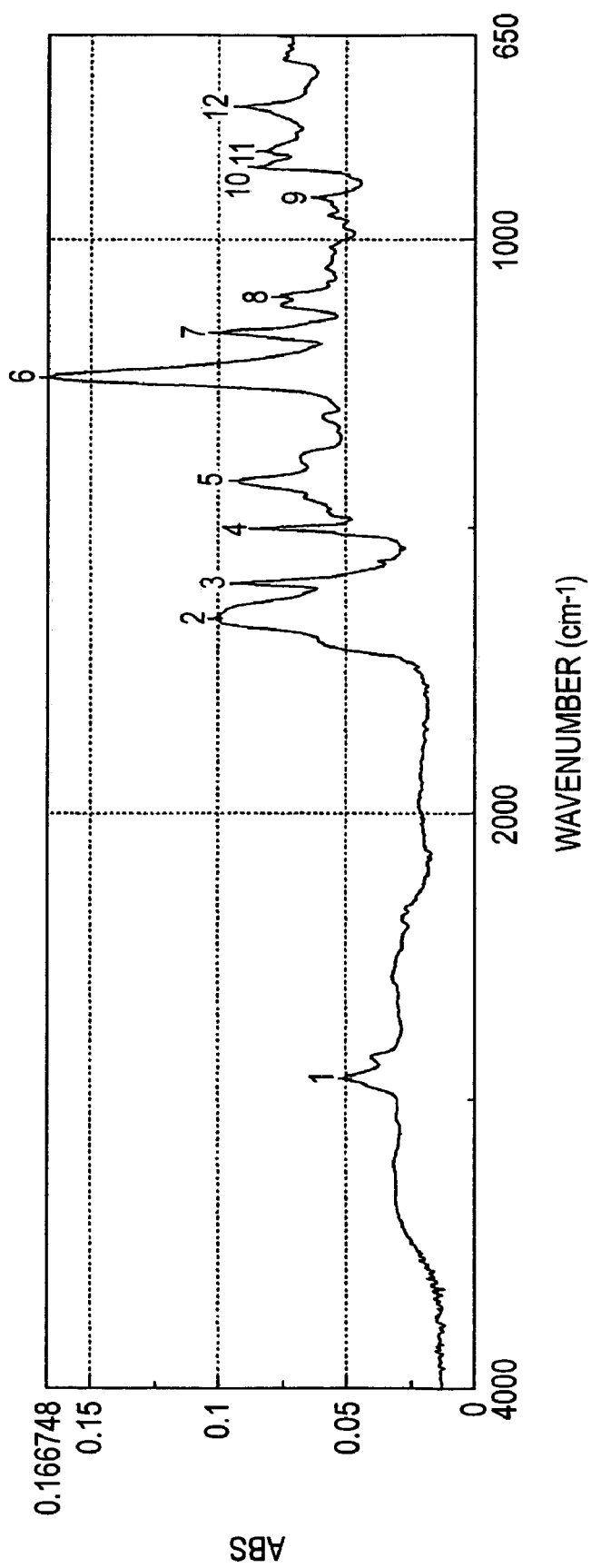
FIG. 14 shows the IR absorption spectrum data of the amorphous obtained in Comparative Example 1.

It was found that the comparative compound thus prepared was amorphous. FIG. 12 shows the powdery X ray diffraction spectrum data of the amorphous substance; FIG. 13 shows the differential scanning calorimetric data thereof; and FIG. 14 shows the IR absorption spectrum data thereof.

(1) Data for Powdery X Ray Diffractometry

Measuring Conditions:
  Apparatus: BRUKER DISCOVER with GADDS (C2)
  Target: Cu
  Filter: no filter
  Voltage: 40 kV
  Current: 40 mA
  Exposure time: 180 sec Results:
  No peak was observed by powdery X ray diffractometry.

(2) Data for Differential Scanning Calorimetry

Measuring Conditions:
  Apparatus: SEIKO INSTRUMENT DSC6200
  Sample weight: 4.0 mg
  Sample cell: SUS sealed container
  Nitrogen gas flow: 20 mL/min
  Temperature elevation rate: 10° C./min Results:
  Consequently, it was shown that the amorphous substance had endothermic peaks around 69 and 248° C.

(3) Data for IR Absorptiometry

Measuring Conditions:
  Apparatus: FTIR-660 plus/SensIR DuraScope manufactured by JASCO CORPORATION
  Resolution: 4 $cm^{-1}$
  Number of scanning: 16 times
  IR (ATR method): 2926, 1659, 1597, 1501, 1418, 1238, 1159, 1098, 928, 876, 849, 774 $cm^{-1}$

EXAMPLE 5(1)-5(9)

Crystals of a Non-Solvate of (3R)-1-butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane Hydrochloride (Crystal A)

By the following procedure, the crystal A as inventive compound were obtained.

EXAMPLE 5(1)

The compound (dry weight of 0.5 g) produced in Reference Example 3 was added to a solution of 6 M hydrochloric acid (0.173 mL) in methanol (4.5 mL). The reaction mixture was dissolved at 60° C. The reaction mixture was cooled down on ice bath. Then water (3 mL) was added to the reaction mixture and was agitated. The precipitated crystals were filtered, and recovered, and then dried to obtain Crystal A with the following physicochemical properties.

Figure 15:
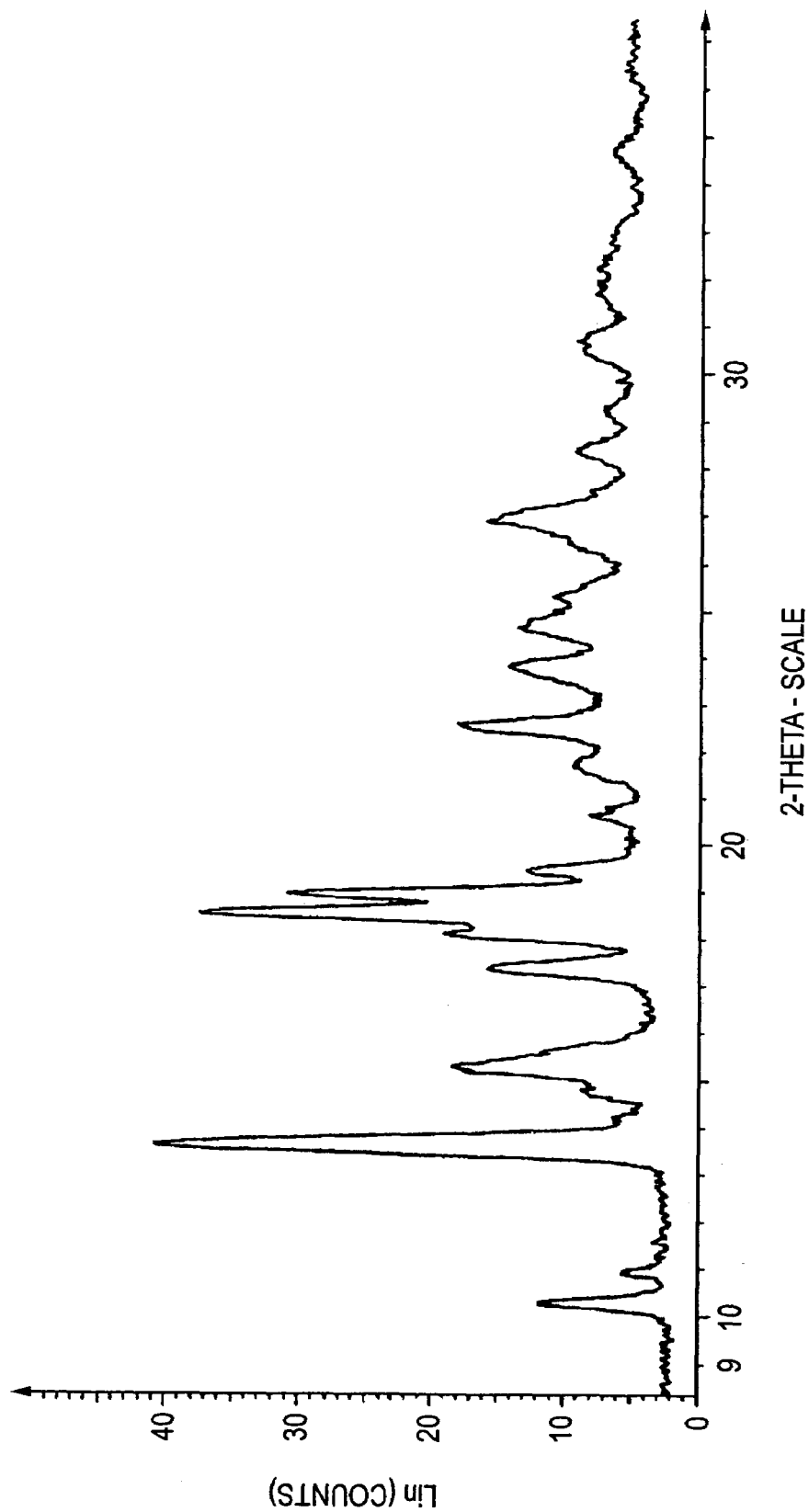
FIG. 15 shows the powdery X ray diffraction spectrum data of Crystal A obtained in Example 5(1).
Figure 16:
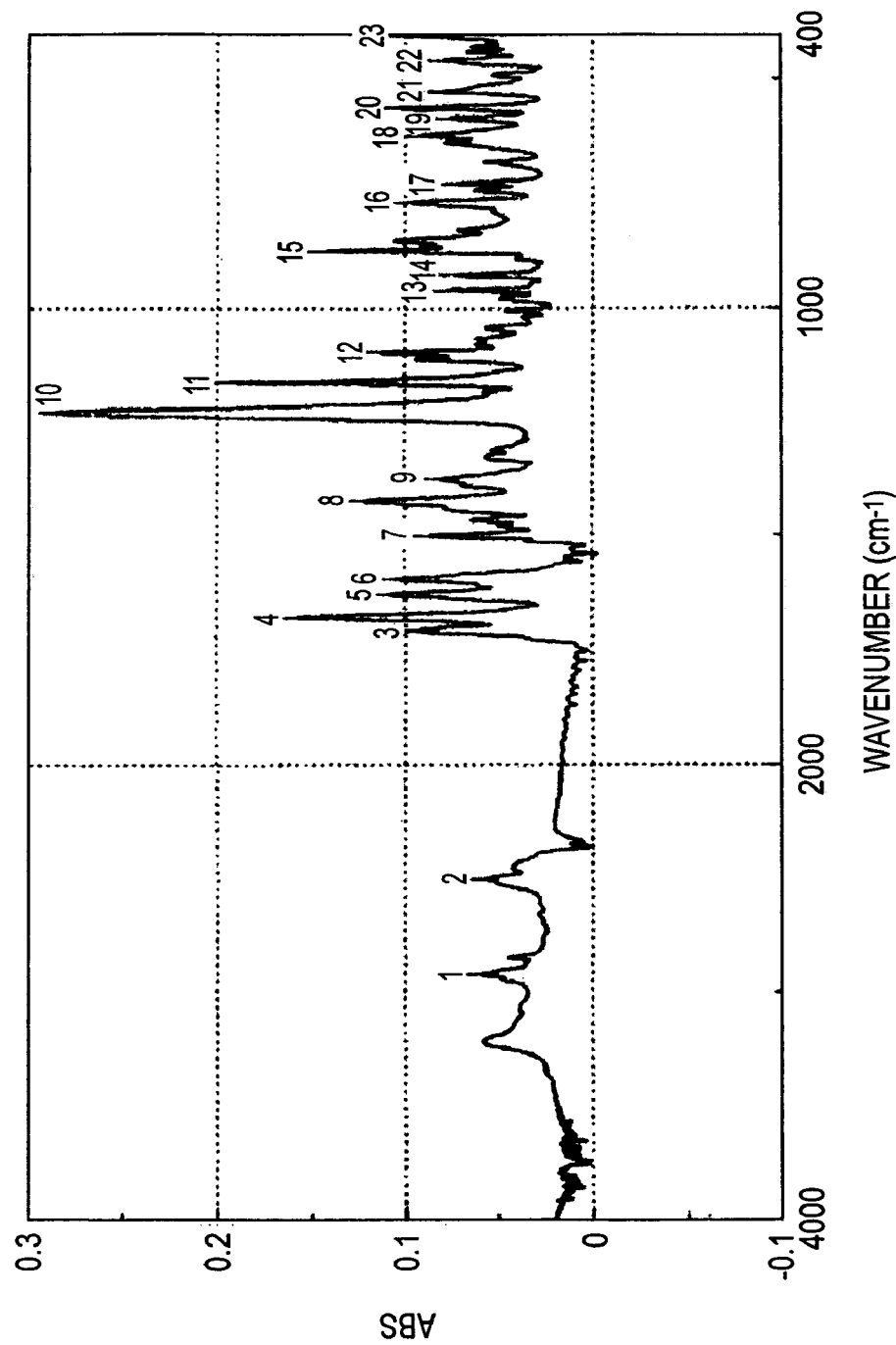
FIG. 16 shows the IR absorption spectrum data of Crystal A obtained in Example 5(1).

FIG. 15 shows the powdery X ray diffraction spectrum data of Crystal A produced in Example 5(1), and FIG. 16 shows the IR absorption spectrum data thereof.

EXAMPLE 5(2)

The compound (dry weight of 0.5 g) produced in Reference Example 3 was added to a solution of 6 M hydrochloric acid (0.173 mL) in methanol (5.25 mL). The reaction mixture was dissolved at 60° C. The reaction mixture was cooled down on ice bath. Then water (2.25 mL) was added to the reaction mixture and was agitated. The precipitated crystals were filtered, and recovered, and then dried to obtain Crystal A with the following physicochemical properties.

Figure 17:
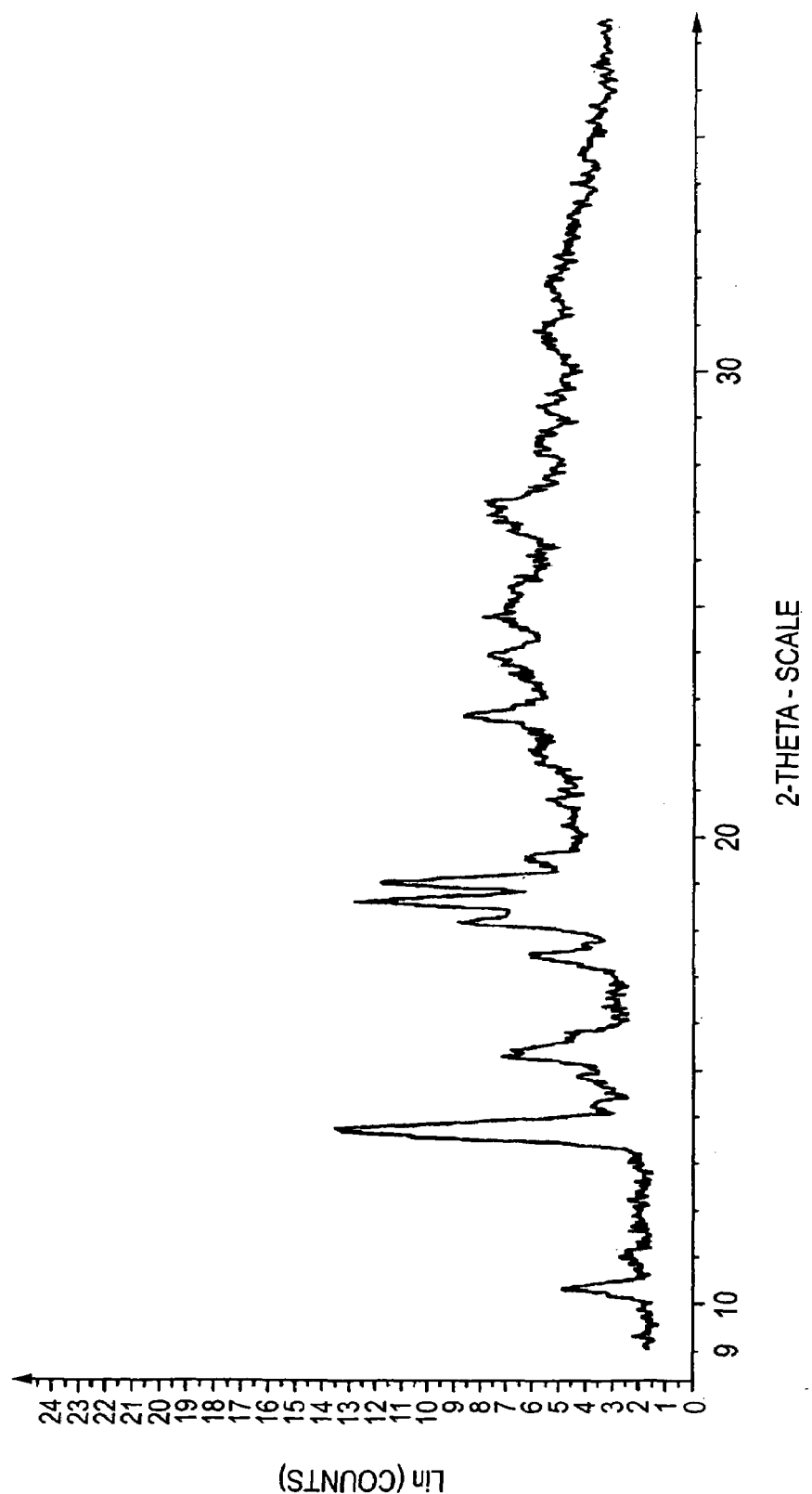
FIG. 17 shows the powdery X ray diffraction spectrum data of Crystal A obtained in Example 5(2).
Figure 18:
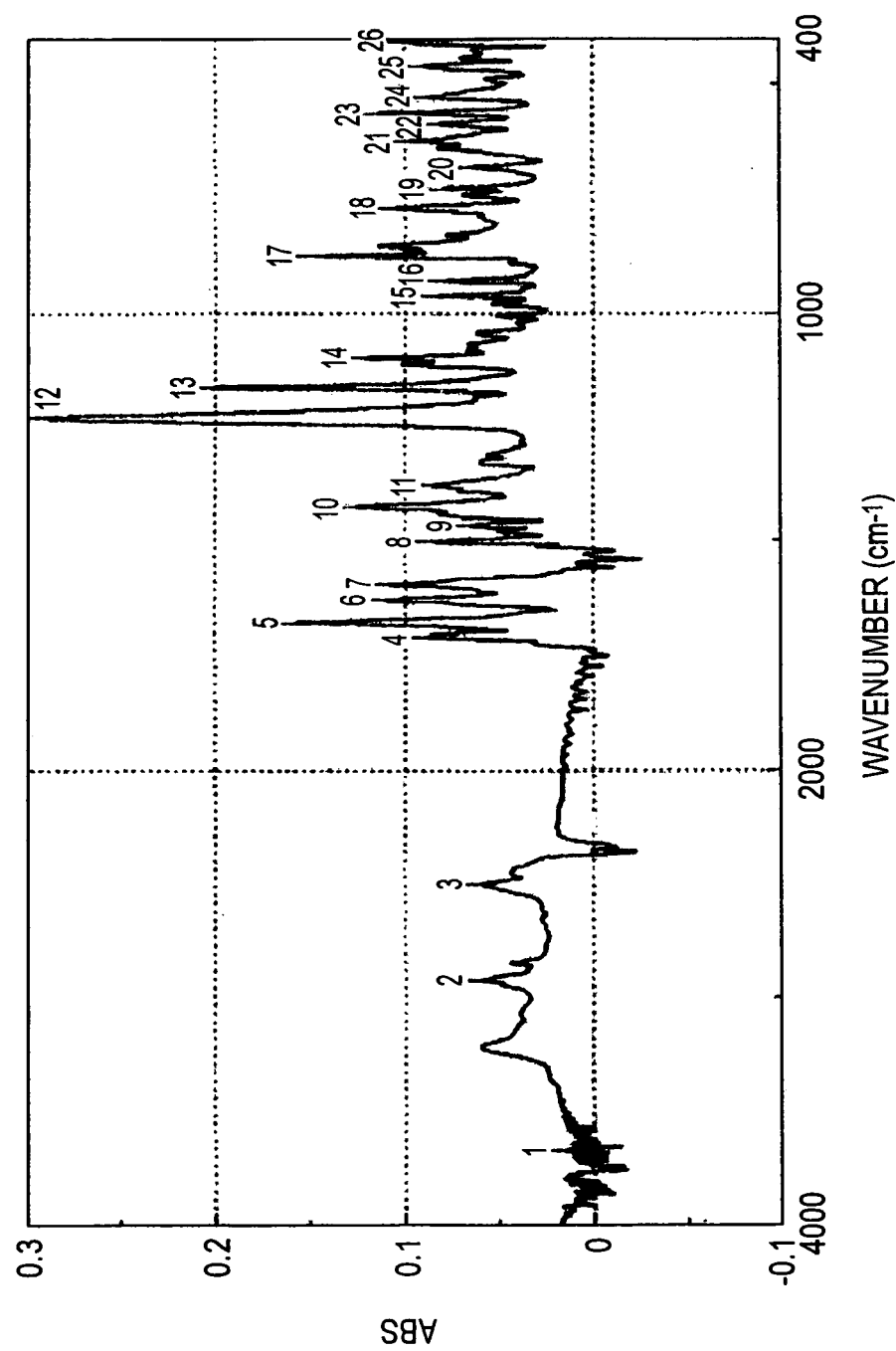
FIG. 18 shows the IR absorption spectrum data of Crystal A obtained in Example 5(2).

FIG. 17 shows the powdery X ray diffraction spectrum data of Crystal A produced in Example 5(2), and FIG. 18 shows the IR absorption spectrum data thereof.

EXAMPLE 5(3)

The compound (dry weight of 0.5 g) produced in Reference Example 3 was added to a solution of 6 M hydrochloric acid (0.173 mL) in methanol (6 mL). The reaction mixture was dissolved at 60° C. The reaction mixture was cooled down on ice bath. Then water (1.5 mL) was added to the reaction mixture and was agitated. The precipitated crystals were filtered, and recovered, and then dried to obtain Crystal A with the following physicochemical properties.

Figure 19:
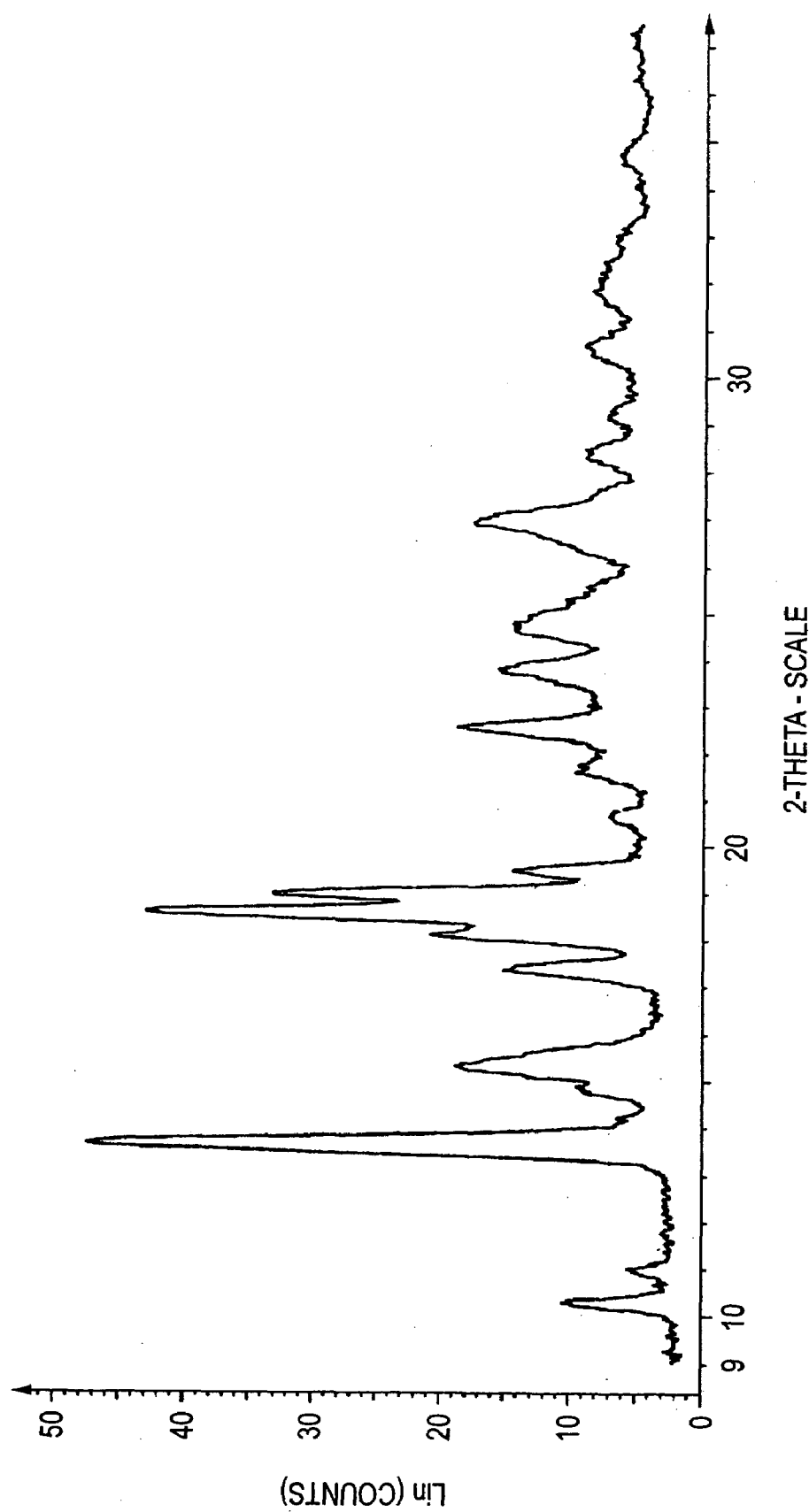
FIG. 19 shows the powdery X ray diffraction spectrum data of Crystal A obtained in Example 5(3).
Figure 20:
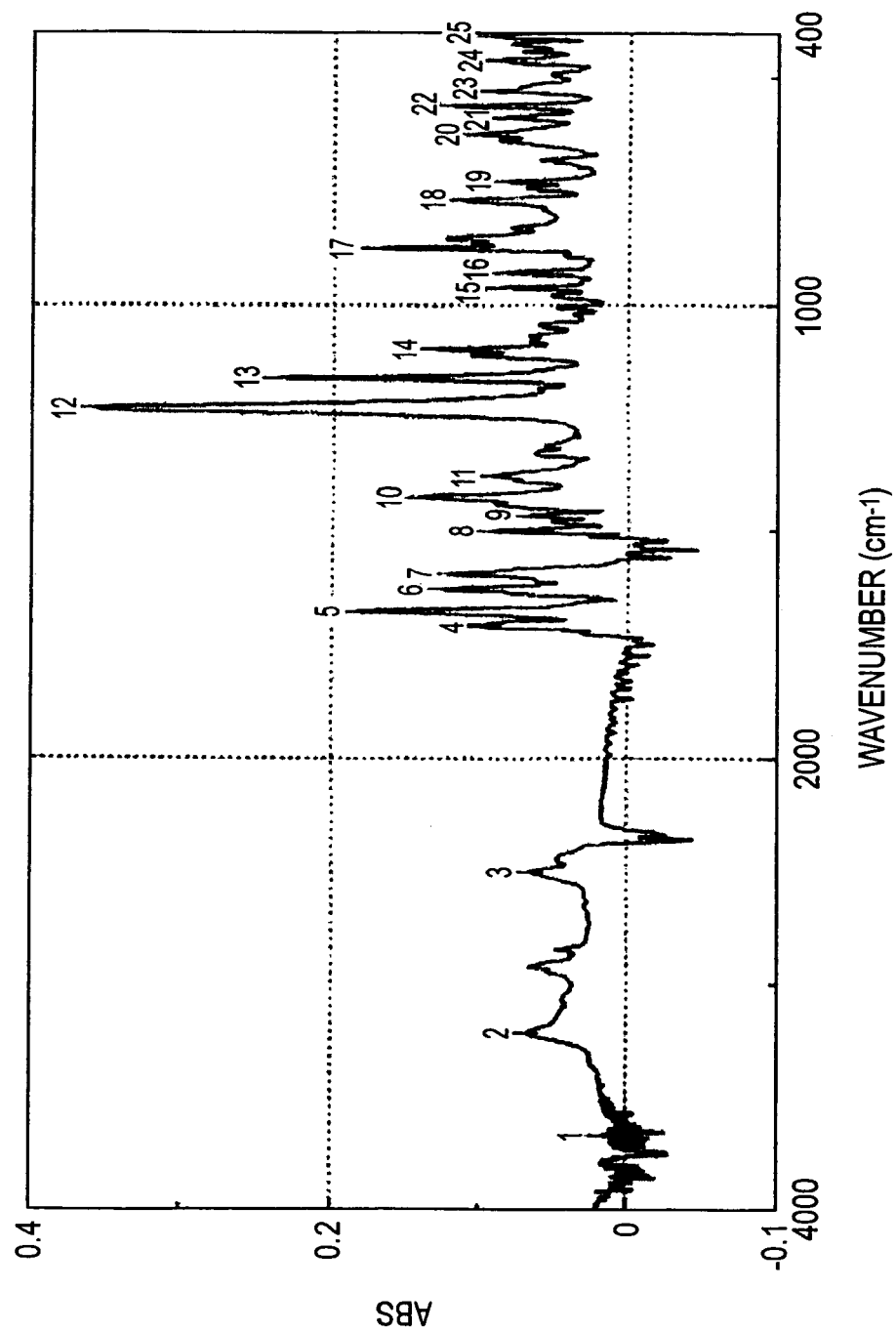
FIG. 20 shows the IR absorption spectrum data of Crystal A obtained in Example 5(3).

FIG. 19 shows the powdery X ray diffraction spectrum data of Crystal A produced in Example 5(3), and FIG. 20 shows the IR absorption spectrum data thereof.

EXAMPLE 5(4)

The compound (dry weight of 1 g) produced in Reference Example 3 was added to a solution of 6 M hydrochloric acid (0.346 mL) and water (2.354 mL) in methanol (6.3 mL). The reaction mixture was dissolved at 51° C. The reaction mixture was cooled down on ice bath. Then methanol (1.8 mL) was added to the reaction mixture and was agitated. Furthermore, water (2.7 mL) was added to the reaction mixture and was agitated. The precipitated crystals were filtered, and recovered, and then dried to obtain Crystal A with the following physicochemical properties.

Figure 21:
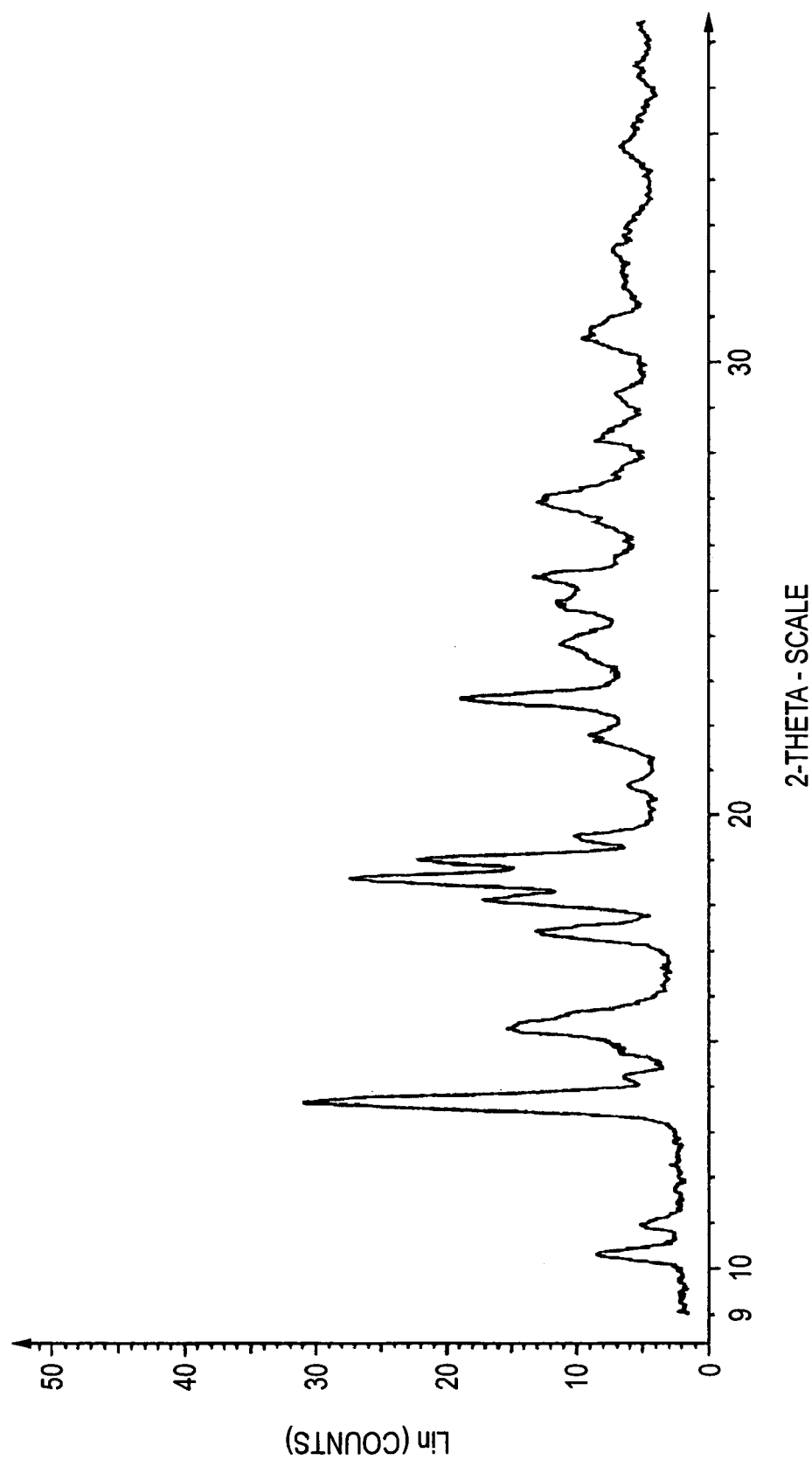
FIG. 21 shows the powdery X ray diffraction spectrum data of Crystal A obtained in Example 5(4).
Figure 22:
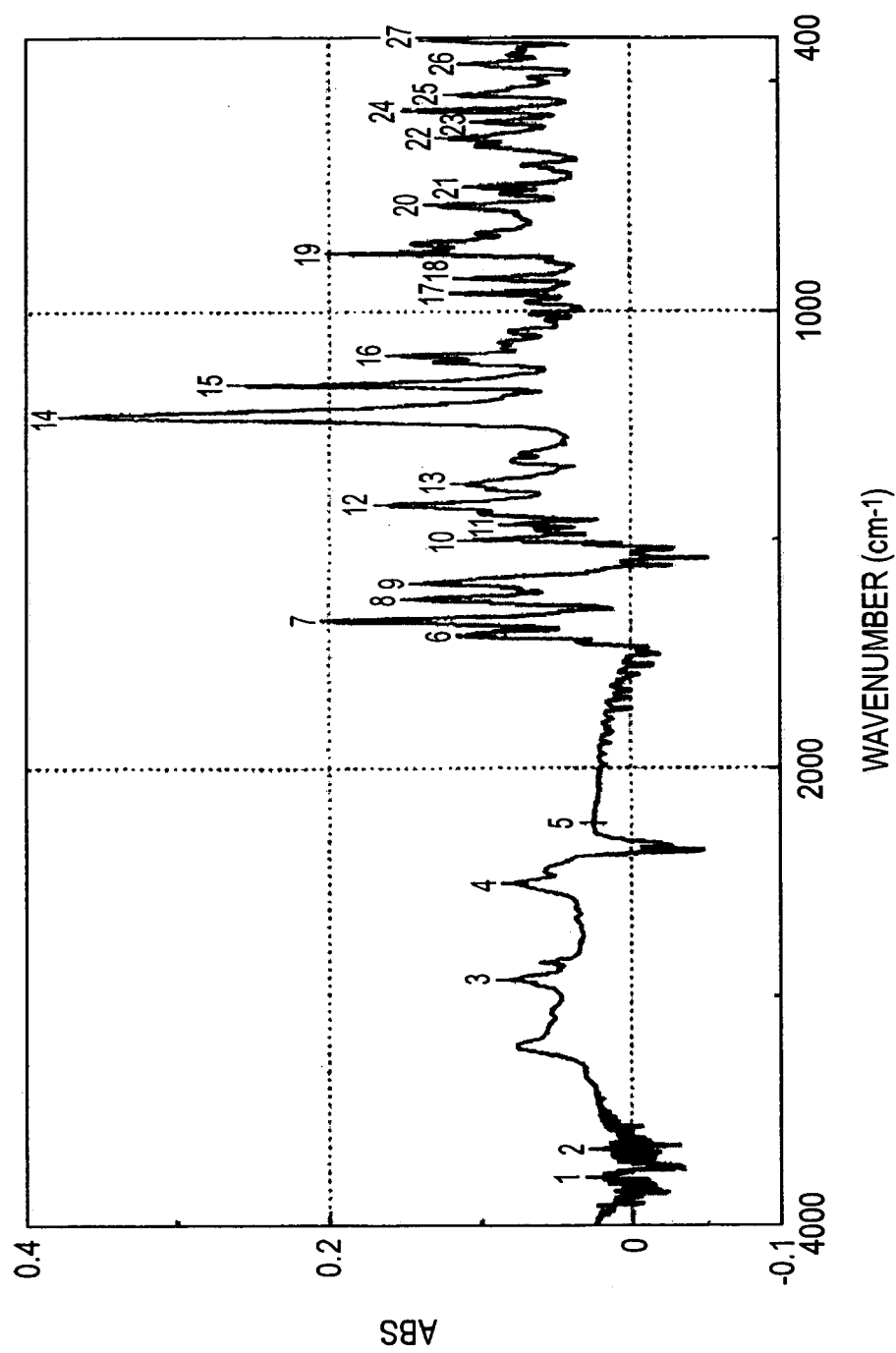
FIG. 22 shows the IR absorption spectrum data of Crystal A obtained in Example 5(4).

FIG. 21 shows the powdery X ray diffraction spectrum data of Crystal A produced in Example 5(4), and FIG. 22 shows the IR absorption spectrum data thereof.

EXAMPLE 5(5)

The compound (dry weight of 1 g) produced in Reference Example 3 was added to a solution of 6 M hydrochloric acid (0.346 mL) and water (4.454 µm) in methanol (7.2 mL). The reaction mixture was dissolved at 57° C. The reaction mixture was cooled down on ice bath. Then methanol (7.2 mL) was added to the reaction mixture and was agitated. The precipitated crystals were filtered, and recovered, and then dried to obtain Crystal A with the following physicochemical properties.

Figure 23:
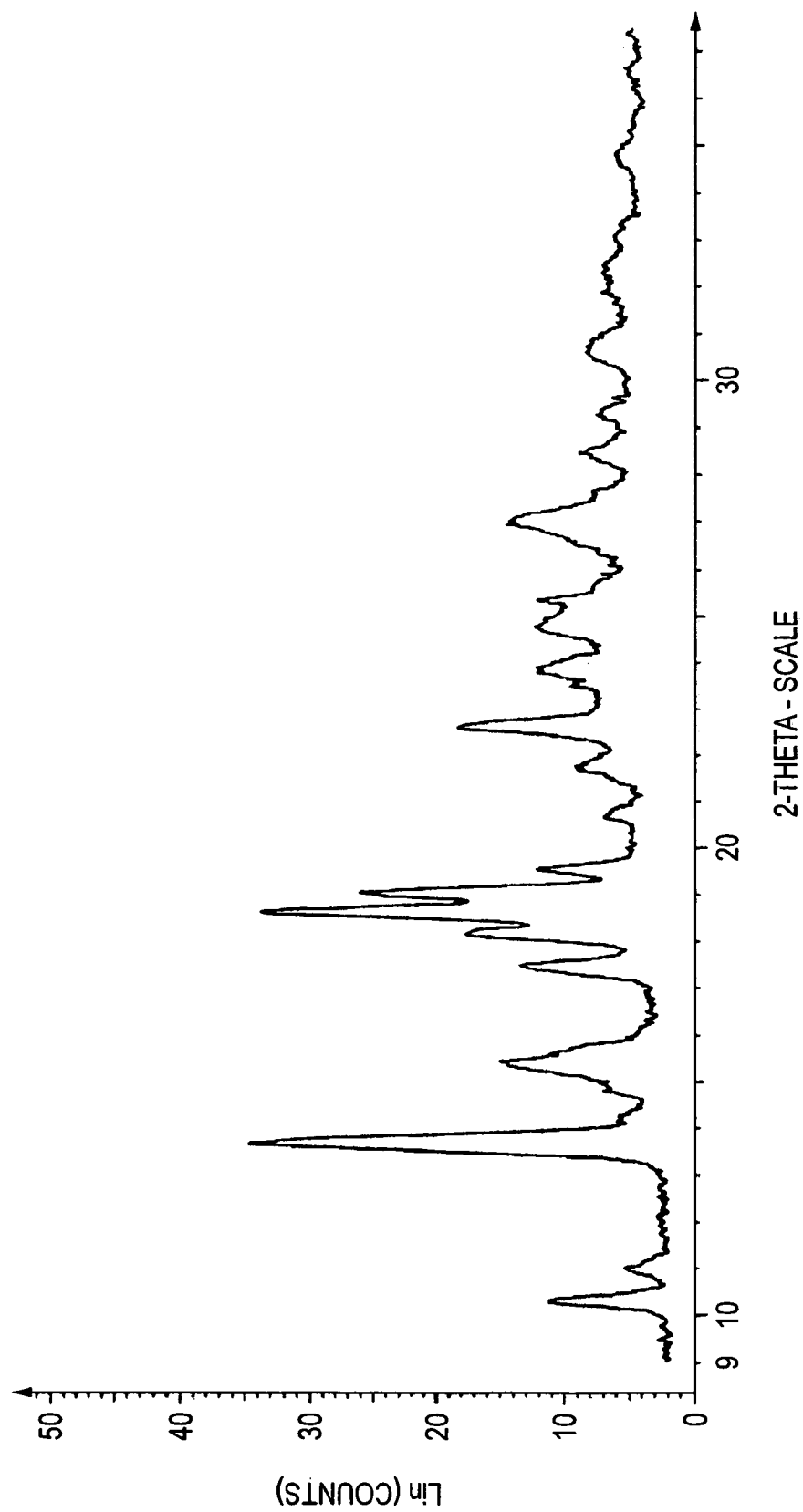
FIG. 23 shows the powdery X ray diffraction spectrum data of Crystal A obtained in Example 5(5).
Figure 24:
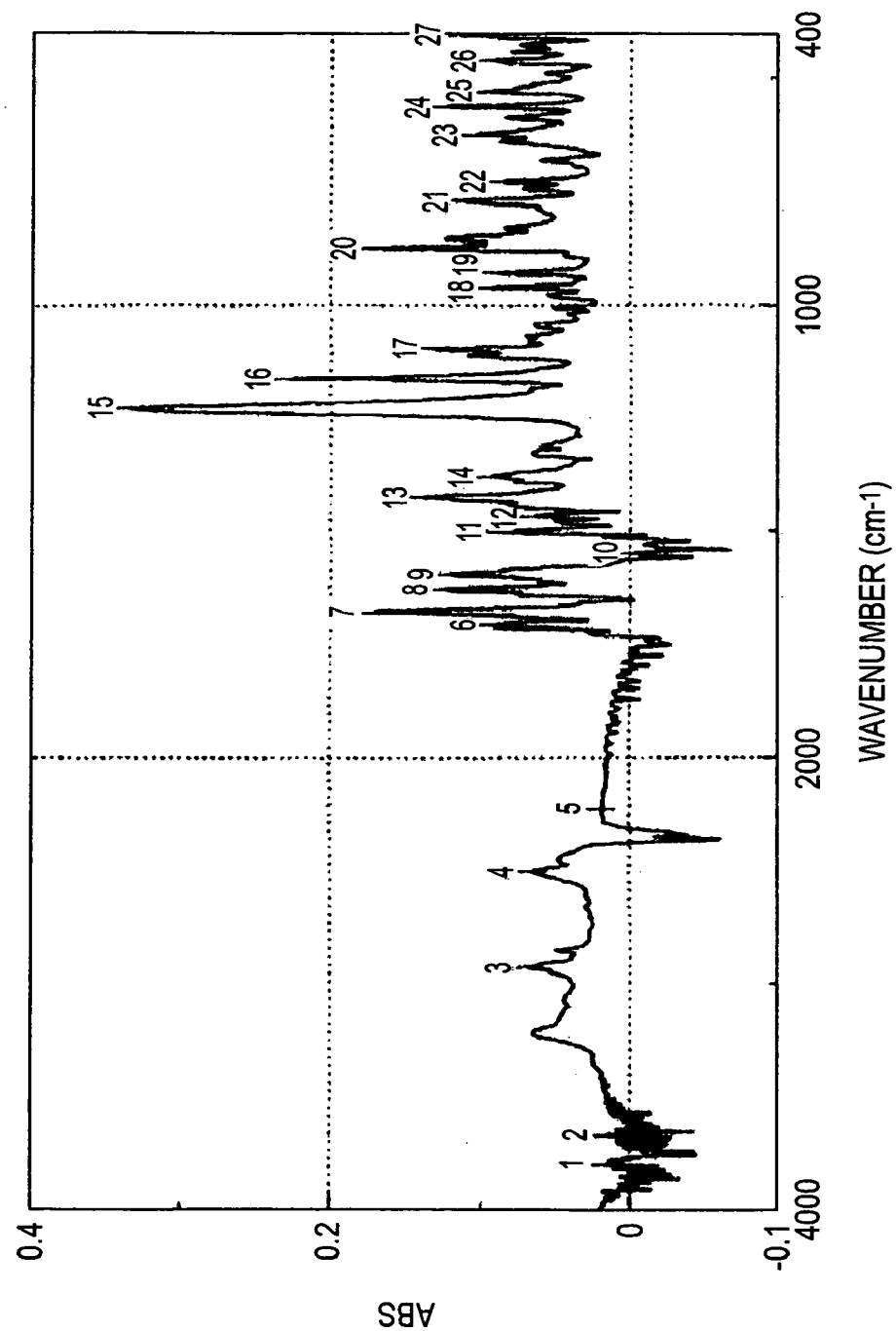
FIG. 24 shows the IR absorption spectrum data of Crystal A obtained in Example 5(5).

FIG. 23 shows the powdery X ray diffraction spectrum data of Crystal A produced in Example 5(5), and FIG. 24 shows the IR absorption spectrum data thereof.

EXAMPLE 5(6)

The compound (dry weight of 6.07 kg) produced in Reference Example 3 was added to a solution of concentrated hydrochloric acid (1.29 kg) and water (15.47 kg) in methanol (30.85 kg). The reaction mixture was dissolved at 52° C. The reaction mixture was cooled down on ice bath. Then methanol (9.7 kg) was added to the reaction mixture and was agitated. Furthermore, water (18 kg) was added to the reaction mixture and was agitated. The precipitated crystals were filtered, and recovered, and then dried to obtain Crystal A with the following physicochemical properties.

Figure 25:
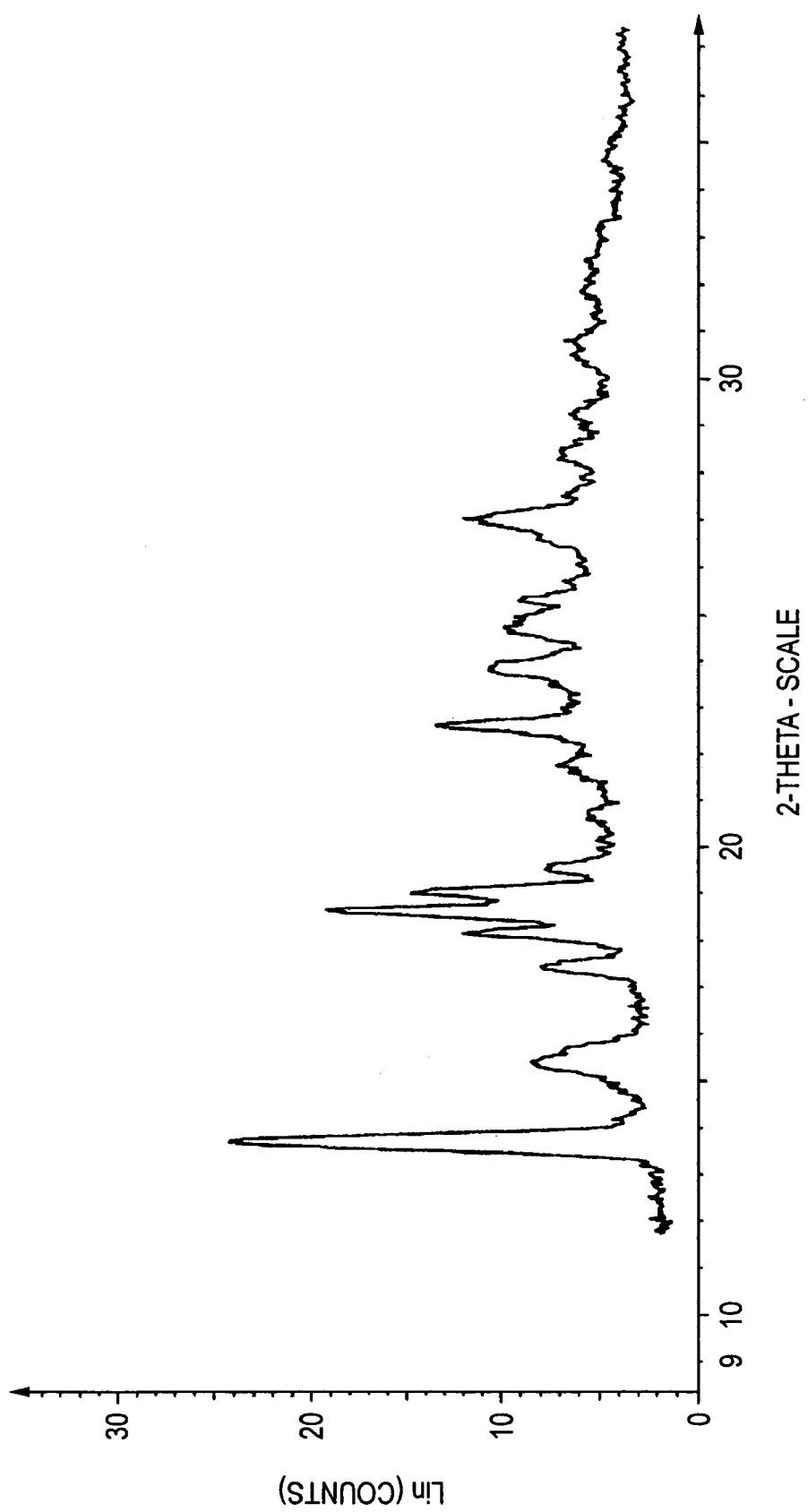
FIG. 25 shows the powdery X ray diffraction spectrum data of Crystal A obtained in Example 5(6).
Figure 26:
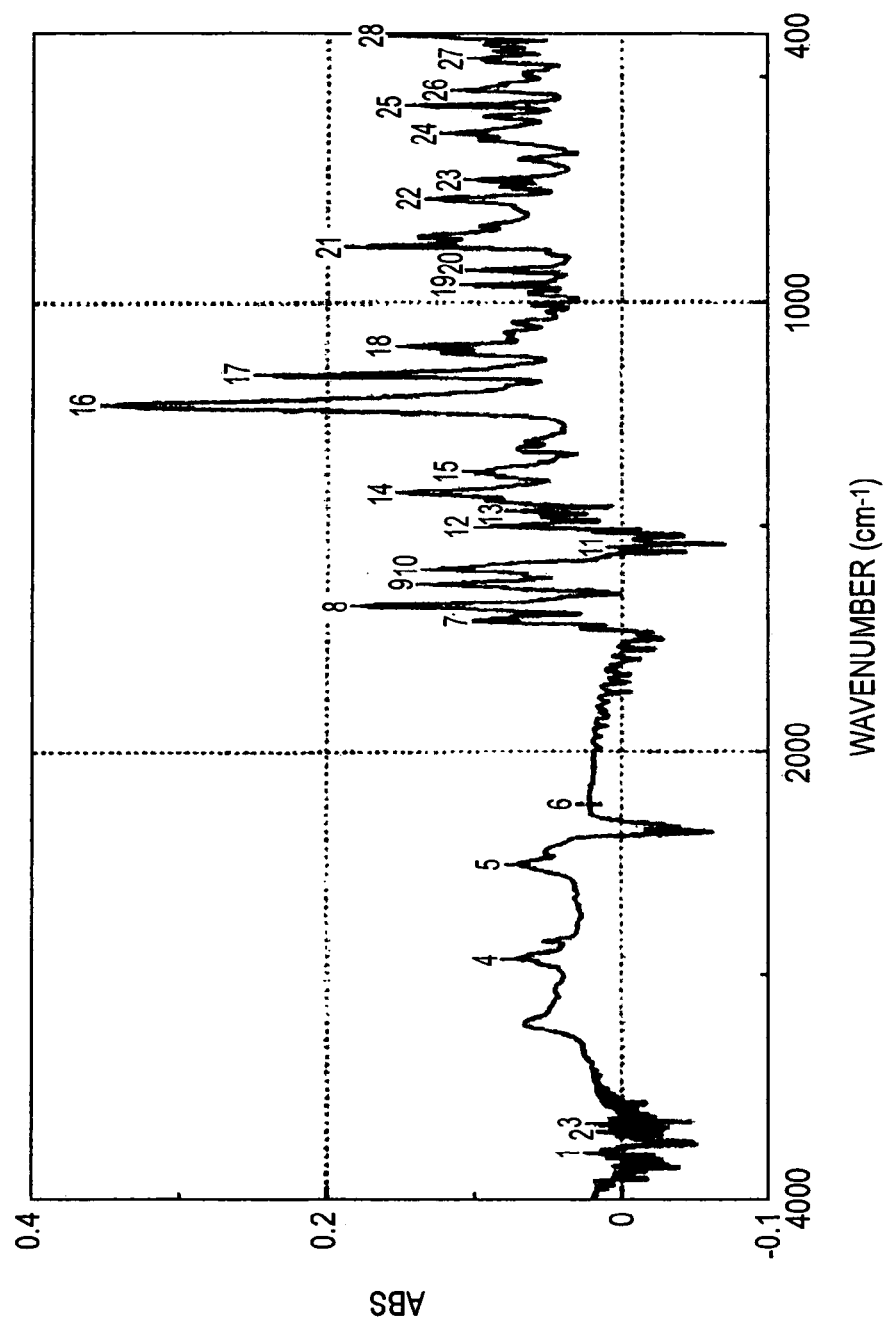
FIG. 26 shows the IR absorption spectrum data of Crystal A obtained in Example 5(6).

FIG. 25 shows the powdery X ray diffraction spectrum data of Crystal A produced in Example 5(6), and FIG. 26 shows the IR absorption spectrum data thereof.

EXAMPLE 5(7)

The compound (dry weight of 91.5 kg) produced in Reference Example 3 was added to a solution of concentrated hydrochloric acid (19.5 kg) and water (237 kg) in methanol (473 kg). The reaction mixture was dissolved at 51° C. The reaction mixture was cooled down on ice bath. Then methanol (150 kg) was added to the reaction mixture and was agitated. Furthermore, water (270 kg) was added to the reaction mixture and was agitated. The precipitated crystals were filtered, and recovered, and then dried to obtain Crystal A with the following physicochemical properties.

Figure 27:
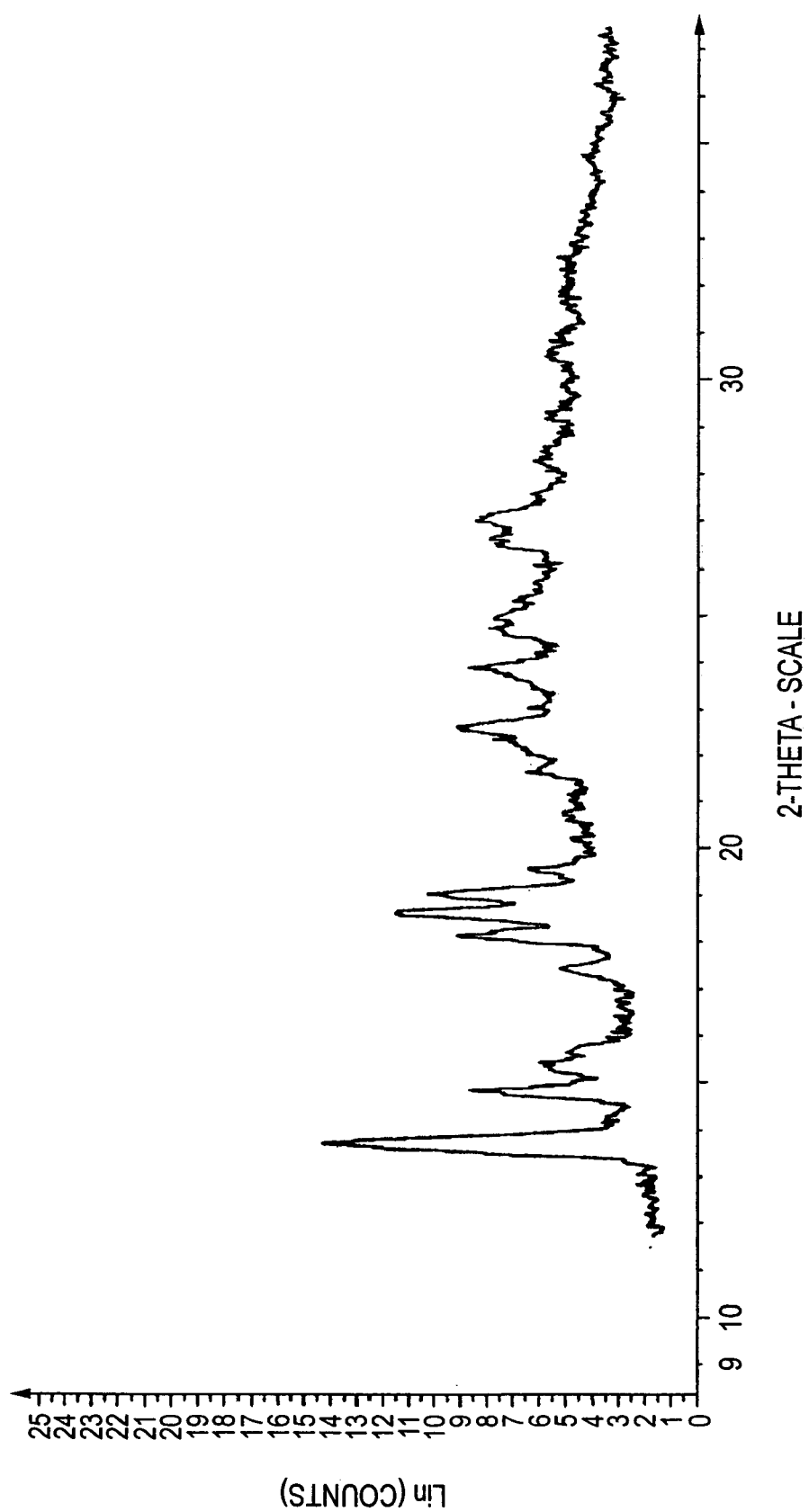
FIG. 27 shows the powdery X ray diffraction spectrum data of Crystal A obtained in Example 5(7).
Figure 28:
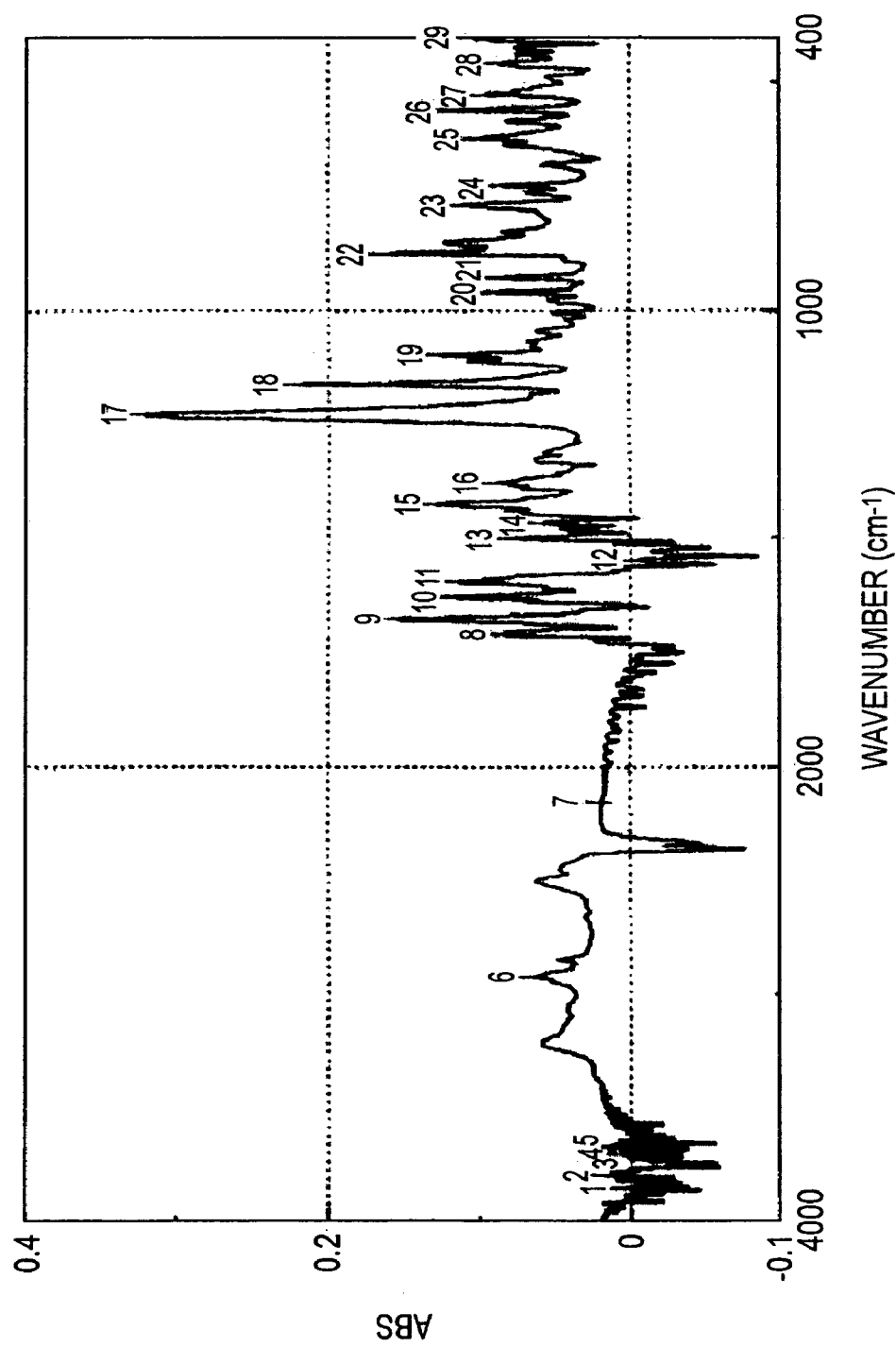
FIG. 28 shows the IR absorption spectrum data of Crystal A obtained in Example 5(7).

FIG. 27 shows the powdery X ray diffraction spectrum data of Crystal A produced in Example 5(7), and FIG. 28 shows the IR absorption spectrum data thereof.

EXAMPLE 5(8)

The compound (dry weight of 322 kg) produced in Reference Example 3 was added to a solution of concentrated hydrochloric acid (68.6 kg) and water (835 kg) in methanol (1645 kg). The reaction mixture was dissolved at 51° C. The reaction mixture was cooled down on ice bath. Then methanol (520 kg) was added to the reaction mixture and was agitated. Furthermore, water (930 kg) was added to the reaction mixture and was agitated. The precipitated crystals were filtered, and recovered, and then dried to obtain Crystal A with the following physicochemical properties.

Figure 29:
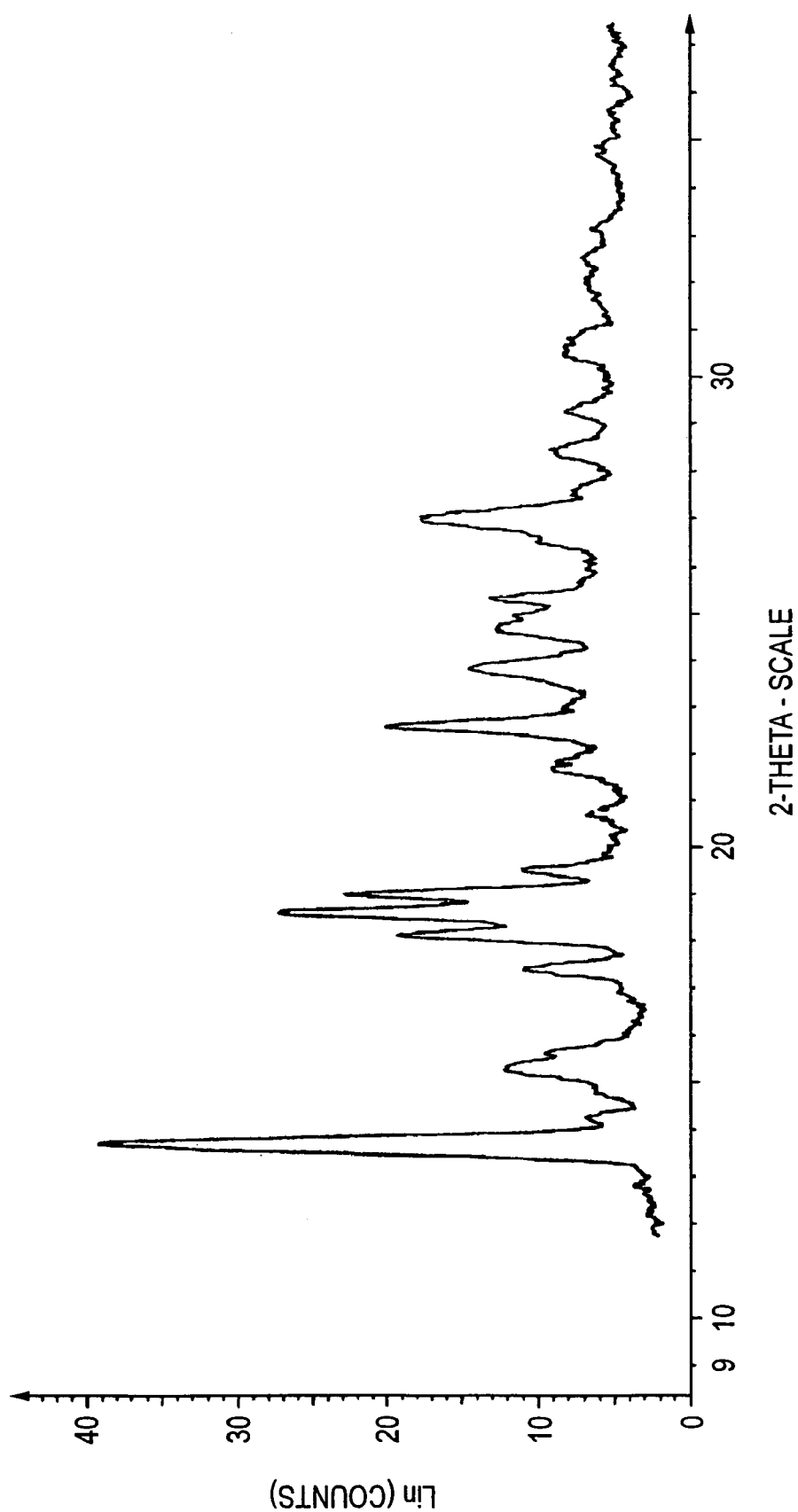
FIG. 29 shows the powdery X ray diffraction spectrum data of Crystal A obtained in Example 5(8).
Figure 30:
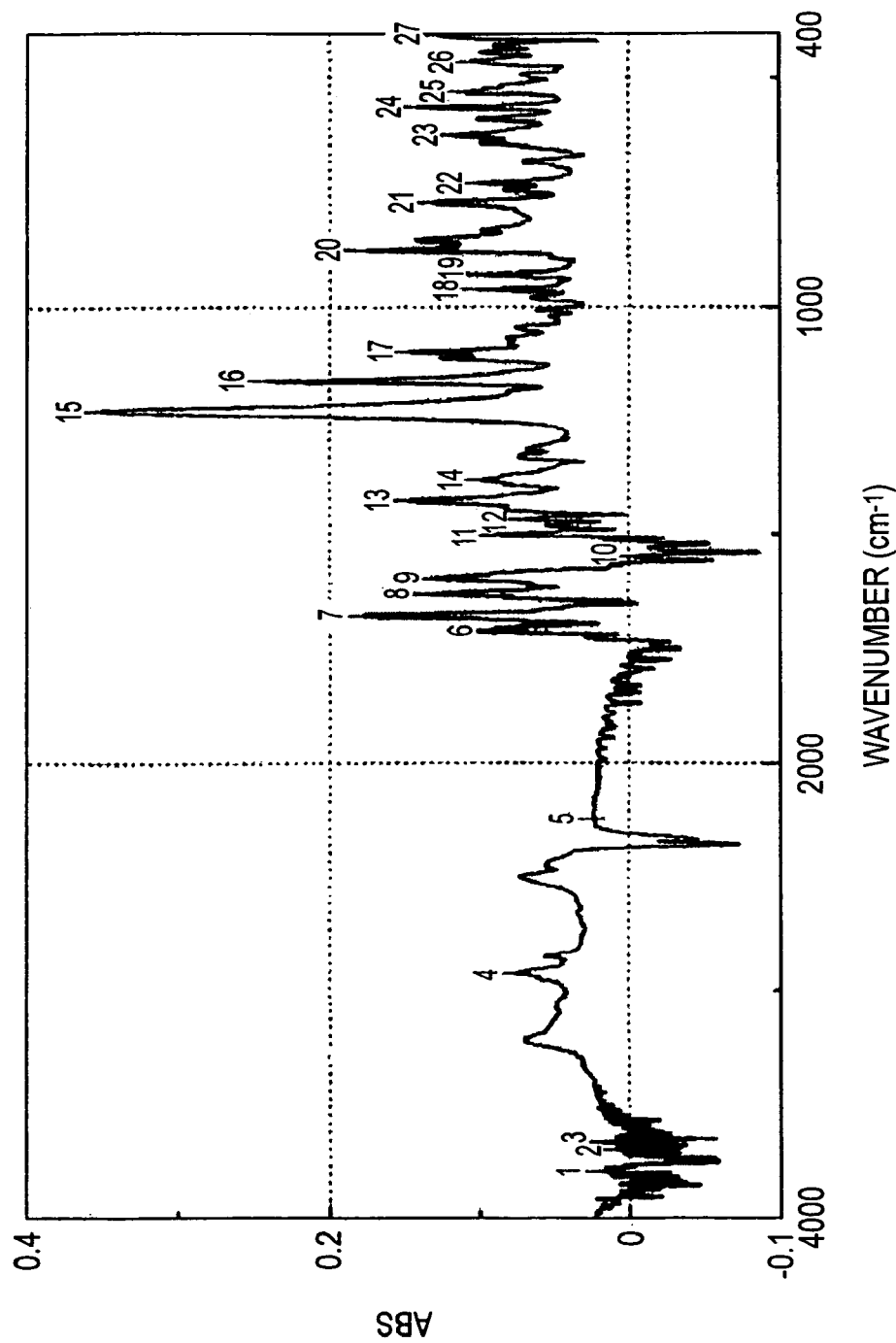
FIG. 30 shows the IR absorption spectrum data of Crystal A obtained in Example 5(8).

FIG. 29 shows the powdery X ray diffraction spectrum data of Crystal A produced in Example 5(8), and FIG. 30 shows the IR absorption spectrum data thereof.

EXAMPLE 5(9)

The compound (dry weight of 157 kg) produced in Reference Example 3 was added to a solution of concentrated hydrochloric acid (33.4 kg) and water (402 kg) in methanol (812 kg). The reaction mixture was dissolved at 52° C. The reaction mixture was cooled down on ice bath. Then methanol (250 kg) was added to the reaction mixture and was agitated. Furthermore, water (460 kg) was added to the reaction mixture and was agitated. The precipitated crystals were filtered, and recovered, and then dried to obtain Crystal A with the following physicochemical properties.

Figure 31:
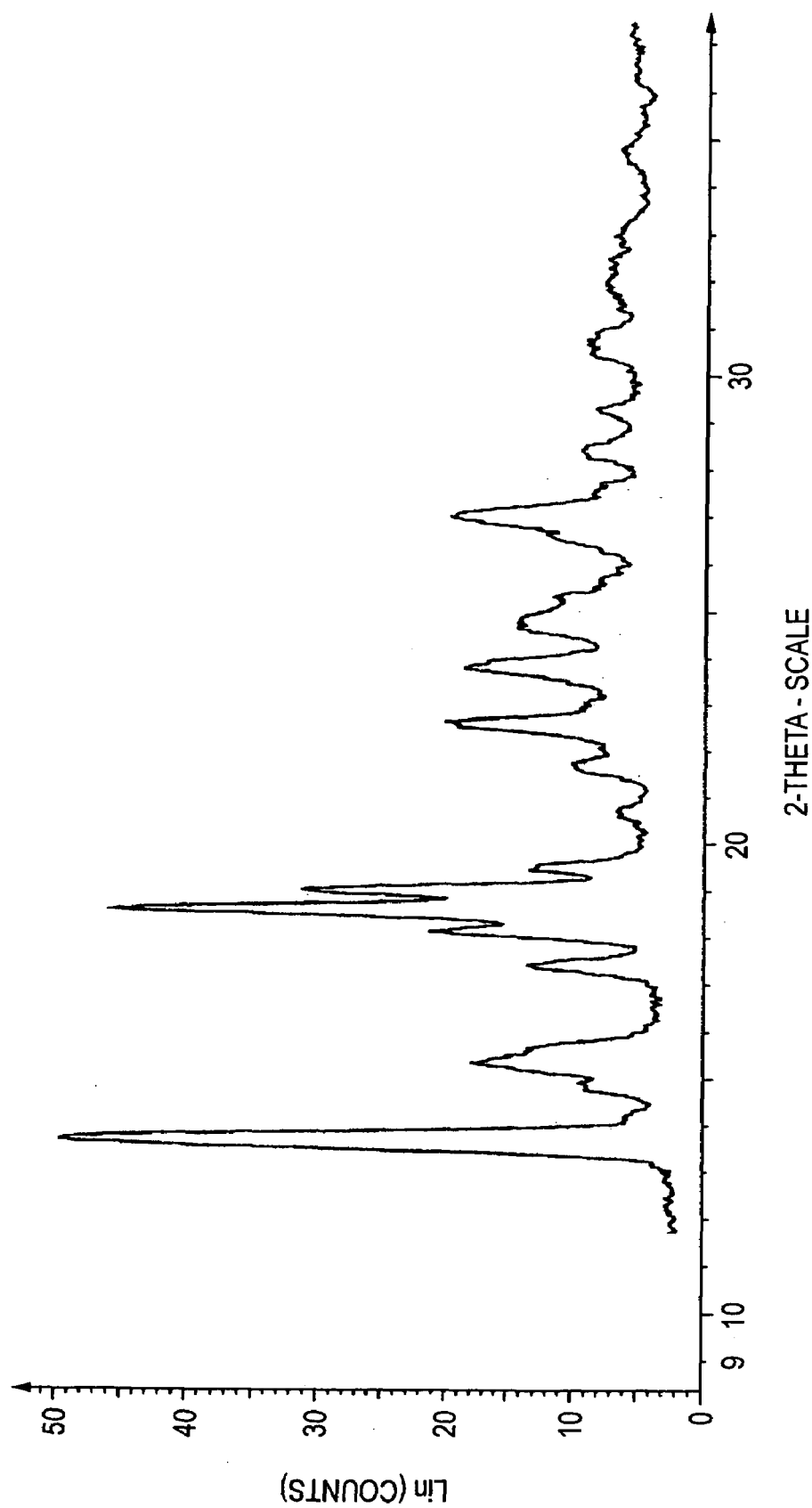
FIG. 31 shows the powdery X ray diffraction spectrum data of Crystal A obtained in Example 5(9).
Figure 32:
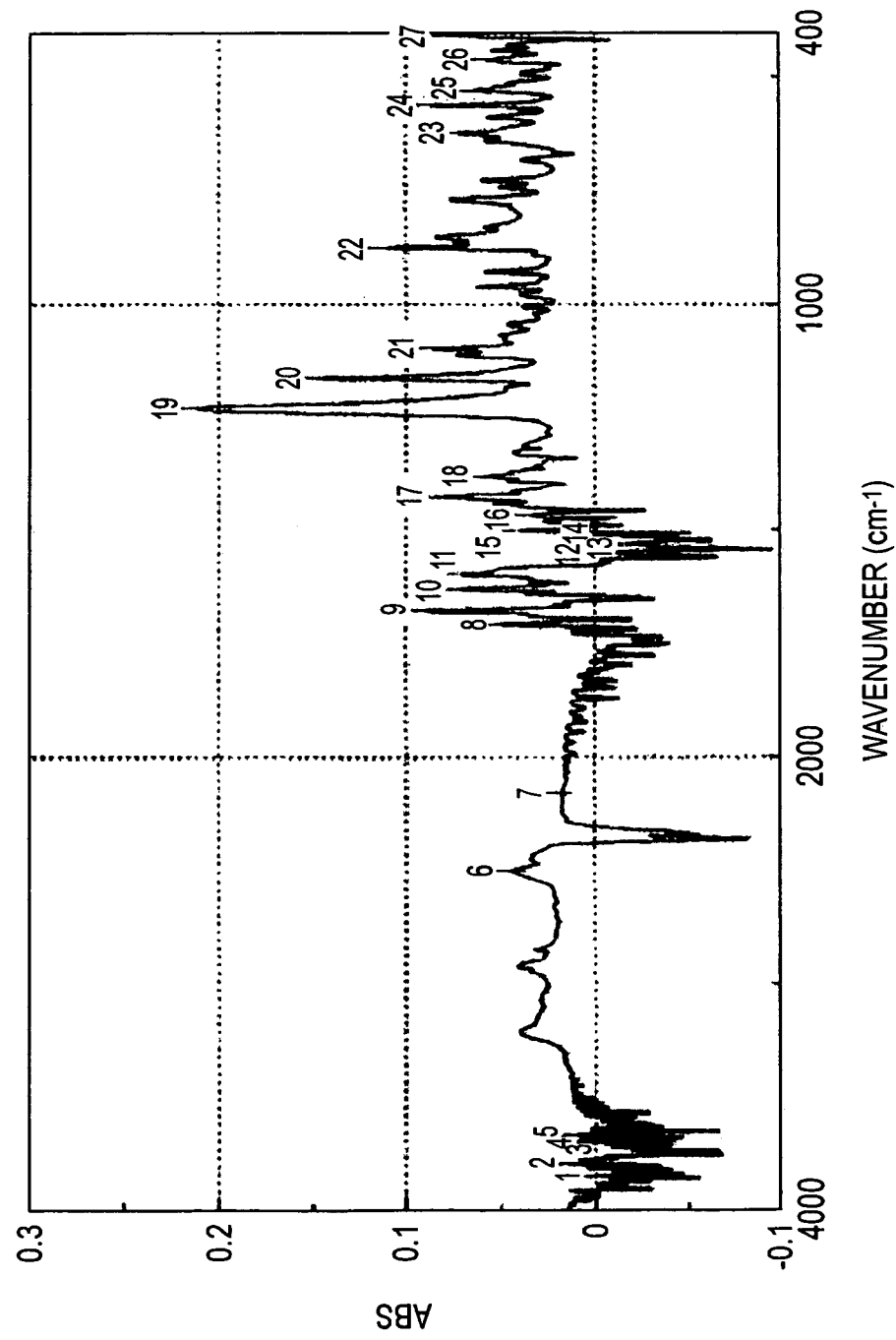
FIG. 32 shows the IR absorption spectrum data of Crystal A obtained in Example 5(9).

FIG. 31 shows the powdery X ray diffraction spectrum data of Crystal A produced in Example 5(9), and FIG. 32 shows the IR absorption spectrum data thereof.

PREPARATION EXAMPLE 1

The following individual ingredients were mixed together according to general methods. The resulting mixture was tableted to prepare 100,000 tablets, each tablet containing 50 mg of the active component.

| | |
|---|---|
| Crystals of (3R)-1-butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane hydrochloride | 5.0 kg |

-continued

| | |
|---|---|
| Carboxy methylcellulose calcium (disintegrator) | 0.2 kg |
| Magnesium stearate (lubricant) | 0.1 kg |
| Microcrystalline cellulose | 4.7 kg |

PREPARATION EXAMPLE 2

The following individual ingredients were mixed together according to the usual method. The resulting solution was sterilized by the usual method and filled in 5-ml portions in ampoules, and freeze-dried by the usual method to obtain 100,000 ampoules, each ampoule containing 20 mg of the active component.

| | |
|---|---|
| Crystals of (3R)-1-butyl-2,5-dioxo-3-[(1R)-1-hydroxy-1-cyclohexylmethyl]-9-[4-(4-carboxyphenyloxy)phenylmethyl]-1,4,9-triazaspiro[5.5]undecane hydrochloride | 2.0 kg |
| Mannitol | 20.0 kg |
| Distilled water: | 500 liters |

The invention claimed is:

1. A crystal of a non-solvate of (3R)-1-butyl-2,5-dioxo-3-((1R)-1-hydroxy-1cyclohexylmethyl)-9-(4-(4-carboxyphenyloxy)phenylmethyl)-1,4,9-triazaspiro[5.5]undecane hydrochloride which has a powdery X ray diffraction spectrum shown in FIG. 1.

2. The crystal according to claim 1, which has diffraction angle 2θ of 5.15, 8.06, 10.26, 11.01, 13.72, 15.46, 17.36, 18.03, 18.58, 19.00, 19.51, 20.71, 21.73, 22.58, 23.80, 24.96 and 27.07 (degree) on the powdery X ray diffraction spectrum.

3. A crystal of a non-solvate of (3R)-1-butyl-2,5-dioxo-3-((1R)-1-hydroxy-1cyclohexylmethyl)-9-(4-(4-carboxyphenyloxy)phenylmethyl)-1,4,9-triazaspiro [5.5]undecane hydrochloride which has an IR absorption spectrum shown in FIG. 3.

4. The crystal according to claim 3, which has absorptions at 2924, 2504, 1682, 1632, 1597, 1503, 1426, 1377, 1235, 1163, 1098, 961, 928, 876, 855, 770, 727 and 681 $cm^{-1}$ on the IR absorption spectrum.

5. The crystal according to claim 1 or 3, which has a mean particle size of about 0.05 µm to about 200 µm.

6. The crystal according to claim 1 or 3, which is a crystal of $P2_1$ space group.

7. The crystal according to claim 6, which has lattice constants of a=11.8105 Å±7%, b=7.8730 Å±7% and c=18.2351 Å±7%.

8. A process for producing a crystal of a non-solvate of(3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane hydrochloride, which comprises carrying out crystallization from a lower alcohol solvent which may contain water or a water-miscible ether solvent which may contain water, in which a crudely purified substance of(3R)-1-butyl-2,5-dioxo-3-((1R)-1-hydroxy-1-cyclohexylmethyl)-9-(4-(4-carboxyphenyloxy)phenylmethyl)-1,4,9-triazaspiro [5.5]undecane hydrochloride is dissolved or suspended.

9. The process according to claim 8, wherein the lower alcohol solvent is $C_{1-4}$ alkyl alcohol or $C_{1-4}$ alkyl acetate.

10. The process according to claim 9, wherein the lower alcohol solvent is methanol or ethanol.

11. The process according to claim 9, wherein the lower alcohol solvent is ethyl acetate.

12. The process according to claim 8, wherein the water-miscible ether solvent is 1,2-dimethoxyethane, dioxane or tetrahydrofuran.

13. The process according to claim 8, wherein the water and the lower alcohol solvent or the water and the water-miscible ether solvent are mixed in a mixing volume ratio of 1:50 to 7:3.

14. The process according to claim 13, wherein the water and the lower alcohol solvent or the water and the water-miscible ether solvent are mixed in a mixing volume ratio of 1:35 to 5:5.

15. The process according to claim 8, wherein the crystallization is carried out at about −10° C. to about 40° C.

16. The process according to claim 8, wherein the crystallization is carried out for about 20 minutes to about 5 hours.

17. A crystal of a non-solvate of (3R)-1-butyl-2,5-dioxo-3-((1R)-1-hydroxy-1-cyclohexylmethyl)-9-(4-(4-carboxyphenyloxy)phenylmethyl)-1,4,9-triazaspiro [5.5]undecane hydrochloride which is obtainable by the process according to claim 13 which has a powdery X ray diffraction spectrum shown in FIG. 1 and which has an IR absorption spectrum shown in FIG. 3.

18. A process for producing a crystal of a non-solvate of (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane hydrochloride, which comprises: dissolving or suspending (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane and hydrogen chloride in a solvent selected from (1) $C_{1-4}$ alkyl alcohol, (2) a mixed solvent of $C_{1-4}$ alcohol and water, (3) a water-miscible ether solvent, (4) a mixed solvent of a water-miscible ether solvent and water, (5) a mixed solvent of $C_{1-4}$ alkyl alcohol and a water-miscible ether solvent, (6) a mixed solvent of $C_{1-4}$ alkyl alcohol, a water-miscible ether solvent and water and (7) water, followed by heating at about 40° C. to about 80° C.; and cooling the resulting mixture at about −5° C. to about 35°0 C.

19. The process according to claim 18, wherein the $C_{1-4}$ alkyl alcohol is methanol or ethanol.

20. The process according to claim 18, wherein the water-miscible ether solvent is 1,2-dimethoxyethane, dioxane or tetrahydrofuran.

21. The process according to claim 18, which comprises: dissolving or suspending (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane and hydrogen chloride in a solvent selected from (1) $C_{1-4}$ alkyl alcohol, (2) a mixed solvent of $C_{1-4}$ alkyl alcohol and water, (3) a water-miscible ether solvent, (4) a mixed solvent of a water-miscible ether solvent and water, (5) a mixed solvent of $C_{1-4}$ alkyl alcohol and a water-miscible ether solvent, (6) a mixed solvent of $C_{1-4}$ alkyl alcohol, a water-miscible ether solvent and water and (7) water, followed by heating at about 40° C. to about 80° C.; cooling the resulting mixture at about −5° C. to about 35° C.; adding $C_{1-4}$ alkyl alcohol or a water-miscible ether solvent to the mixture; and optionally adding water to the mixture.

22. A process for producing a crystal of a non-solvate of (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5]undecane hydrochloride, which comprises dissolving or suspending a solvate of (3R)-1-butyl-2,5-dioxo-3-((1R)-1-hydroxy-1-cyclohexylmethyl)-9-(4-(4- carboxyphenyloxy)phenylmethyl)-1,4,9-triazaspiro[5.5] undecane hydrochloride or amorphous (3R)-1-butyl-2,5-dioxo-3-((1R)-1-hydroxy-1-cyclohexylmethyl)-9-(4-(4-carboxyphenyloxy)phenylmethyl)-1,4,9-triazaspiro[5.5] undecane hydrochloride in $C_{1-4}$ alkyl acetate, followed by heating at about 40° C. to about 80° C.; and cooling the resulting mixture at about −5° C. to about 35° C.

23. A crystal of a non-solvate of (3R)-1-butyl-2,5-dioxo-3-((1R)-1-hydroxy-1-cyclohexylmethyl)-9-(4-(4-carboxyphenyloxy)phenylmethyl)- 1,4,9-triazaspiro [5.5]undecane hydrochloride which is obtainable by the process according to claim 18 which has a powdery X ray diffraction spectrum shown in FIG. 1 and which has an IR absorption spectrum shown in FIG. 3.

24. The crystal according to claim 23, which has a mean particle size of about 0.05 μm to about 200 μm.

25. The crystal according to claim 1 or 3, which has a melting point of about 230° C. to about 240° C.

26. The crystal according to claim 1 or 3, which has a melting point of about 232° C. to about 235° C.

* * * * *